US005418165A

United States Patent [19]

McBeath

[11] Patent Number: 5,418,165

[45] Date of Patent: May 23, 1995

[54] COLD TOLERANT TRICHODERMA

[75] Inventor: Jenifer H. McBeath, Fairbanks, Ak.

[73] Assignee: The University of Alaska-Fairbanks, Fairbanks, Ak.

[21] Appl. No.: 983,518

[22] Filed: Apr. 19, 1993

Related U.S. Application Data

[63] Continuation-in-part of Ser. No. 570,270, Aug. 20, 1990, abandoned.

[30] Foreign Application Priority Data

Aug. 19, 1991 [AR] Argentina ........................ 320431
Aug. 19, 1991 [NZ] New Zealand ........................ 239452
Aug. 20, 1991 [MX] Mexico ........................ 00741

[51] Int. Cl.[6] ........................ A01N 63/00; C12N 15/00; C12N 1/14

[52] U.S. Cl. ........................ 435/256.7; 435/172.1; 424/93.5

[58] Field of Search ........................ 435/71.1, 172.1, 256.7; 424/93 Q, 93.5

[56] References Cited

U.S. PATENT DOCUMENTS 4,489,161 12/1984 Papavizas et al. .................. 435/254
4,713,342 12/1987 Chet et al. .................. 435/254
4,748,021 5/1988 Chet et al. .................. 424/93
4,797,361 1/1989 Montenecourt .................. 435/198
4,828,600 5/1989 McCabe et al. .................. 71/76
4,847,284 7/1989 Schwartz et al. .................. 514/424
4,915,944 4/1990 Chet et al. .................. 435/254
4,931,352 6/1990 Fromtling et al. .................. 435/71.3

FOREIGN PATENT DOCUMENTS 0059176 9/1982 European Pat. Off. ..... A01N 63/04
0124388 11/1984 European Pat. Off. ....... C12N 1/14
0133878 3/1985 European Pat. Off. ..... A01N 63/04

OTHER PUBLICATIONS

Rifai, M. 1969, Mcycological Papers 116:1–56.
Karsten, Hedwegia, 31:292–296 (1892).
Baker, Tibtech, 7:34–38 (1989).
Tronsmo et al., J. Cell. Biochem., 13A:177 (1989).
Kohl et al., J. Phytopathol., 125:320–326 (1989).
Kohl et al., Agnew Botanik, 62:(5–6):301–309 (1988).
Papavizas, Phytopathology, 72(1):126–132 (1982).
Donsch, Compendium of Soil Fungi, pp. 795–807 (1980).

*Primary Examiner*—David T. Fox
*Attorney, Agent, or Firm*—Finnegan, Henderson, Farabow, Garrett & Dunner

[57] ABSTRACT

The invention includes a new, cold tolerant strain of mycoparasite Trichoderma and mutants that are resistant to a pesticide to which the Trichoderma isolate is sensitive. These novel Trichoderma are capable of parasitizing fungi which are pathogenic to plants. They are also capable of producing proteinaceous, antimycotic substances which can inhibit the growth of plant pathogenic fungi. Cold tolerant Trichoderma and its biotypes can be used in, but not limited to, controlling fungal plant disease.

6 Claims, 17 Drawing Sheets

FIG. 10

| TEMP. °C | COLONY REACHING 9cm DIA. ON OATMEAL AGAR |
|---|---|
| 4° | > 30 DAYS |
| 7° | 9 DAYS |
| 10° | 7 DAYS |
| 17° | 4 DAYS |
| 25° | 3 DAYS |
| 30° | 4 DAYS |
| 32° | 7 DAYS |
| 33° | 10 DAYS |

COLD TOLERANT TRICHODERMA

CROSS-REFERENCE TO RELATED APPLICATIONS

This application is a continuation-in part of application Ser. No. 07/570,270, which was filed, Aug. 20, 1990, now abandoned, the entire specification of which is relied upon and specifically incorporated herein by reference.

BACKGROUND OF THE INVENTION

This invention relates to a new isolate of a cold tolerant Trichoderma species (hereafter "the Trichoderma isolate"). This invention also relates to mutants of the Trichoderma isolate that are resistant to commercially available pesticides, such as Benomyl and Ridomil.

This invention further relates to a method for the control of the transmission and spread of plant disease by applying an agriculturally effective amount of cold tolerant Trichoderma or a pesticide resistant cold tolerant Trichoderma mutant to a plant or plant tissue to be protected from a fungal pathogen. This invention also relates to a method for the treatment of plant disease by applying an agriculturally effective amount of the Trichoderma isolate or a pesticide resistant mutant of the Trichoderma isolate to a plant or plant tissue to be treated.

This invention still further relates to a method of promoting the growth and development of a plant by applying an agriculturally effective amount of the Trichoderma isolate or Benomyl resistant mutants of the Trichoderma isolate to a plant or plant tissue.

This invention also relates to three molecules associated with the Trichoderma isolate, that are useful for the control and treatment of plant disease.

Plant pathogens such as soil-borne pathogenic fungi are well recognized agricultural problems causing extensive damage, including damping off, white rot, wilt, southern rot, snow mold, root rot, black scurf, and grey mold to various commercially important crops. For example, these fungi have been found to cause extensive damage to wheat, barley, oats, grasses, cotton, potatoes, tomatos, peas, vegetables, flowers, grapes, strawberries, pistachio, almond, apples, cherries, peaches, nectarines, pears, persimmons, plums, prunes, olives, walnuts, trees, and shrubs and thus pose serious problems to the agriculture, horticulture, and forestry industries. In the past the major approach in controlling these pathogens has been through the use of chemical pesticides. However, due to important economic and ecologic considerations, their use has been disfavored and alternative approaches are sought.

Recently, the biological control ("biocontrol") of plant pathogens has been achieved. For example, the control of many pathogenic fungi through the use of antagonistic microorganisms has been demonstrated for several species of Trichoderma. While it has been found that different species or strains within a species of Trichoderma may be differentially antagonistic to different pathogenic fungi, *Trichoderma viride* and *Trichoderma harzianum* have been shown to be generally effective as biocontrol agents. Some of the possible advantages associated with the biocontrol of pathogenic fungi through the application of Trichoderma as compared to the use of chemical pesticides include an improvement in food safety, a reduction of pollution in the environment, and a decreased incidence of occupational disease to workers in the industry.

The usefulness of *T. viride* and *T. harzianum* is greatly limited in certain situations due to their intolerance to low temperatures. Because many plant pathogens, such as Pythium spp., are most destructive in cool soils, the inability of these Trichoderma species to grow and function in these soils leaves the plants without protection at the time of greatest need. It would be desirable, therefore, to obtain a microorganism that has the characteristics of *T. viride* and *T. harzianum* as biocontrol agents and yet be sufficiently capable to withstand cold temperatures to function as biocontrol agents in cool soils.

Such a cold-tolerant biocontrol agent would be especially useful in high-latitude regions. By way of example, snow mold, a disease caused by low temperature pathogenic fungi, is the major cause of crop failures of winter cereals, such as wheat, rye, triticale, and barley, making it very difficult to establish a winter cereal industry in Alaska as well as other high-latitude regions.

The organisms *Sclerotinia borealis, Fusarium nivale*, sclerotial low temperature basidiomycete (sLTB), *Coprinus psychromobidus* (i.e., low temperature basidiomycete-LTB) and Typhula spp. are implicated as the most prevalent causative agents of this fungal disease. These fungi infect host plants in late fall or winter when the soil is not yet frozen. During the long winters in the dark, humid conditions found under a thick snow layer, the fungi proliferate and spread in the host tissues. This parasitic relationship between the host and the parasitic fungi results in the rapid depletion of nutrient reserves, destruction of plant cells by extracellular enzymes, and the eventual death of the host plants. Consequently, the effective control of snow mold disease through the application of a cold tolerant Trichoderma may very well permit farmers in Alaska or other areas where the growing season is short to cultivate new crops, such as winter cereals.

There is a need, therefore, in the art for a biocontrol agent that is effective against snow mold as well as other plant diseases caused by pathogenic fungi at low temperature.

There also exists a need for a biocontrol agent that would be generally effective against fungal plant pathogens that exist under more moderate conditions as well as at low temperatures. The number and variety of fungi that are plant pathogens under moderate conditions is extensive. Among the Phycomycetes examples of important plant pathogens are Pythium which causes damping off, *Peronospora* tabacina which causes blue mold of tobacco, and *Phytophthora infestans* which causes late blight of potato. Among the Basidiomycetes examples of plant pathogens include Armillaria sp. which causes root rot and Typhula spp. which causes snow mold. Among the Ascomycetes, examples of plant pathogens include *Sclerotinia sclerotiorum* and *S. borealis* which cause white rot and snow mold, respectively. Among the Deuteromycetes examples of important plant pathogens include Botrytis sp., Verticillium sp., Fusarium sp., Sclerotium sp., and *Rhizoctonia solani* which are responsible for plant diseases such as wilt disease on fruit trees, vegetables, and potatoes, white rot diseases of beans, carrots, and onions, gray mold of fruits and seedlings, root rot, black scurf and damping off.

Consequently, there exists a need in the art for a biocontrol agent that is effective against a wide range of pathogenic fungi existing at moderate as well as low temperatures.

SUMMARY OF THE INVENTION

This invention aids in fulfilling the needs in the art by providing a biologically pure cold tolerant Trichoderma isolate, CHS 861 (ATCC 74015). This invention provides a method to promote the growth and development of a plant or plant tissue by applying an agriculturally effective amount of Trichoderma isolate CHS 861 (ATCC 74015) to a plant or plant tissue. Plant tissues would include, for example, fruits, seeds, or seedlings. This invention also provides a method to control the transmission and spread of plant disease by applying an agriculturally effective amount of the Trichoderma isolate CHS 861 (ATCC 74015) to a plant or a plant tissue to be protected from a fungal pathogen. This invention can also be used to treat a plant infected with a fungal pathogen by applying an agriculturally effective amount of the Trichoderma isolate CHS 861 (ATCC 74015). In another embodiment of this invention, the Trichoderma isolate CHS 861 (ATCC 74015) may be applied to a plant to be protected from a fungal pathogen in admixture with a commercially available pesticide such as Ridomil or a Ridomil-like pesticide to which the Trichoderma isolate is resistant. In specific embodiments of this invention, the fungal pathogens to be controlled are *Armillaria mellea, Botrytis cinerea, F. nivale, Coprinus psychromobidus* (LTB), sLTB, Pythium spp., *Rhizoctonia solani, S. borealis, Typhula incarnata, T. idahoensis, T. ishikariensis, Verticillium dahliae, Sclerotinia sclerotiorum, Sclerotium rolfsii,* and *Sclerotium cepivorum.*

A further aspect of this invention is to provide a biologically pure, cold-tolerant Trichoderma mutant that is resistant to commercially available pesticides such as Benomyl or a Benomyl-like pesticide. Examples of Benomyl resistant mutants are Biotype 453 (ATCC 74016), Biotype 603 (ATCC 74018), and Biotype 901 (ATCC 74017). This invention also provides a method to control the transmission and spread of plant disease, the method comprises applying an agriculturally effective amount of the Benomyl resistant Trichoderma mutants, for example, to a plant or plant tissue to be protected from a fungal pathogen. These Trichoderma isolates can be applied in admixture with, for example, a Benomyl or a Benomyl-like pesticide, to a plant to be protected. This invention also provides a method to promote the growth and development of a plant or plant tissue by applying an agriculturally effective amount of a Trichoderma mutant to a plant or plant tissue.

In specific embodiments, this invention provides a method to treat plant disease by applying an agriculturally effective amount of a Trichoderma mutant as described above to a plant or plant tissue infected with a fungal pathogen, such as *A. mellea, B. cinerea, F. nivale, C. psychromobidus* (LTB), sLTB, Pythium spp., *R. solani, S. borealis, T. incarnata, T. idahoensis, T. ishikariensis, V. dahliae, S. sclerotiorum, S. rolfsii,* and *S. cepivorum.*

In another specific embodiment, this invention provides 2 heat stable proteins derived from a crude culture filtrate of the Trichoderma isolate CHS 861 (ATCC 74015) or the crude culture filtrate of Biotype 603 (ATCC 74018). The proteins have a molecular weight of about 17 kDa and 21 kDa respectively, are associated with cold tolerant Trichoderma, inhibit the growth of sLTB and *Botrytis cinerea*, Pythium spp., *S. sclerotiorum, S. rolfsii,* and *S. cepivorum,* and are in biologically pure form. In a further embodiment these proteins are in a purified form essentially free of other Trichoderma proteins.

In another specific embodiment, this invention provides an additional molecule derived from a crude culture filtrate of the Trichoderma isolate 861 and 453. This molecule has a molecular weight between about 5 kDa and 10 kDa as determined by ultrafiltration, inhibits the growth of sLTB and Botrytis cinerea and is in biologically pure form. In a further embodiment this 5–10 kDa molecule is essentially free of other Trichoderma proteins.

BRIEF DESCRIPTION OF THE DRAWINGS

FIG. 10: A comparison of the effect of temperature on the growth of Trichoderma (ATCC 74015).

DETAILED DESCRIPTION OF THE PREFERRED EMBODIMENTS

Figure 1:
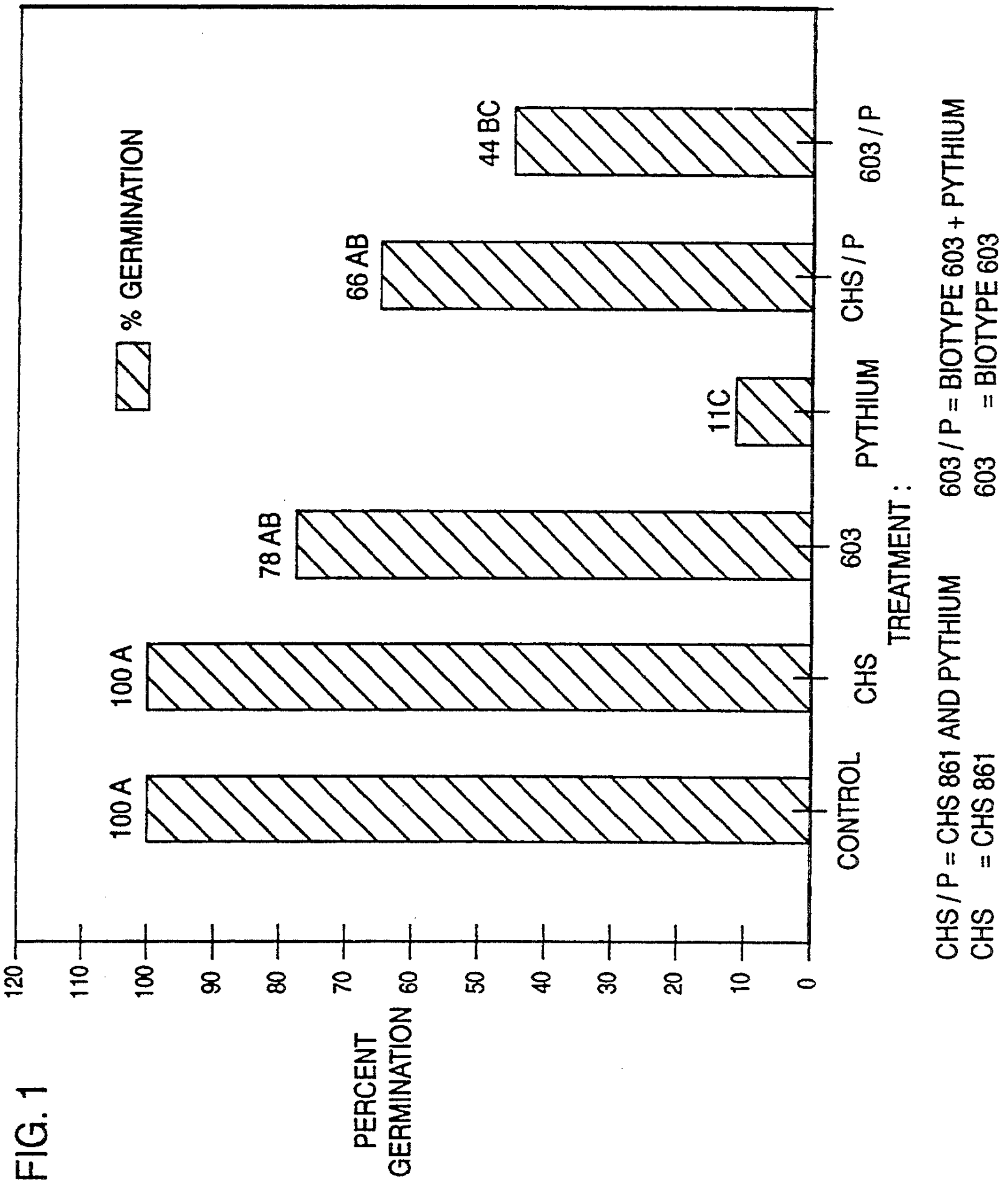
FIG. 1: A comparison of the effect of the Trichoderma isolate CHS 861 (ATCC 74015) and a mutant thereof, Biotype 603 (ATCC 74018), on the germination of pea seeds infected with Pythium spp.

This invention relates to a cold-tolerant Trichoderma isolate and Benomyl resistant mutants thereof that can effectively control low temperature pathogenic fungi and other pathogenic fungi and protect plants from diseases caused by such pathogens. This invention also relates to a method of treating infected plants or plant tissues, a method of controlling the spread of pathogenic fungi at low temperatures as well as under more moderate conditions, and a method of promoting the growth of plants or plant tissues using the cold-tolerant Trichoderma isolate or its mutants. This invention further relates to molecules that effectively control the growth, development, and proliferation of pathogenic fungi at low temperatures as well as under more moderate conditions.

As used herein, the term "cold-tolerant" in the context of the Trichoderma isolate or its mutants refers to the ability of these microorganisms to become well-established and grow with a normal morphology at a temperature less than about 10° C., for example, at about 4° C.

As used herein the term "plant tissue" refers to any tissue derived from a plant at any stage during the life cycle of a plant. By way of example, the term "plant tissue" would include the fruit, seed, or seedling of a plant, or any of the cells derived from fruit, seeds, or seedlings when propagated in tissue culture.

As used herein, the term "pathogenic fungi" refers to fungi which are capable of detrimentally affecting the growth or viability of a plant or plant tissue. "Low-temperature pathogenic fungi" refers to fungi, which are capable of detrimentally affecting the growth or viability of a plant or plant issue at a temperature less than about 10° C., for example, at about 4° C. As used herein, the term "other pathogenic fungi" refers to fungi which are capable of detrimentally affecting the growth or viability of a plant or plant tissue and are not "low-temperature pathogenic fungi as defined supra. As used herein with reference to temperature, the term "more moderate conditions" indicates a temperature greater than about 10° C.

As used herein, the term "biologically pure" refers to a degree of chemical purity wherein impurities that substantially affect the functional properties of the purified component have been substantially removed.

As used herein the term "agriculturally effective amount" refers to an amount of an active agent that is sufficient to produce the desired agricultural effect. For example, in the case of Trichoderma, an "agriculturally effective amount" of Trichoderma would be that amount necessary to provide plant growth, control the transmission of plant disease, or effectively treat plant disease.

As used herein, the term "Benomyl or Benomyl-like pesticide" refers to 1-(butylcarbomyl)-2-benzimidazole carbamate or a compound that is a homolog of Benomyl or exhibits substantially the same functional properties as Benomyl.

As used herein, the term "Ridomil or Ridomil-like pesticide" refers to N-[2,6-dimethylphenyl]-N-[methoxyacetyl]-alanine methyl ester or a compound that is a homolog of Ridomil or exhibits substantially the same functional properties as Ridomil.

As used herein, the term "antibiotic" refers to a substance such as a compound, e.g. protein, mixture or microorganism that is capable of destroying or inhibiting the growth of another microorganism such as bacteria or fungi. As used herein, the term "antimycotic" is an antibiotic that is capable of destroying or inhibiting the growth of a fungi. As used herein, the term "antibacterial" is an antibiotic that is capable of destroying or inhibiting the growth of a bacteria.

The cold-tolerant Trichoderma isolate, CHS 861 (ATCC 74015), is deposited with the American Type Culture Collection, Rockville, Md., 20852, pursuant to the provisions of the Budapest Treaty on the International Recognition of the Deposit of Microorganisms for the Purposes of Patent Procedure, under accession number ATCC-74015.

The cold-tolerant Benomyl resistant Trichoderma isolates, Biotype 453 (ATCC 74016), Biotype 603 (ATCC 74018), and Biotype 901 (ATCC 74017), are similarly deposited with the American Type Culture Collection under accession numbers ATCC-74016, ATCC-74018, and ATCC-74017, respectively.

The cold tolerant Trichoderma isolates antagonistic to low temperature pathogenic fungi have been isolated and identified. Soil samples, collected at 66 sites throughout Interior and Southcentral Alaska were sprinkled on Trichoderma semiselective medium (TSM) (G. C. Papavizas, *Phytopathol.* 72:121-125 (1982); the contents of which are hereby incorporated by reference) and were incubated at about 7° C. for about 10 days. Mycelia from each colony on TSM were viewed, and those that displayed the typical characteristics of Trichoderma such as unusually fine mycelia and green-colored spore mass were transferred to slants of Potato Dextrose agar (PDA) (DIFCO Laboratory). After incubation at about 25° C. for about 10 days, the isolates that showed no signs of contamination were subcultured on V-8 juice agar plates as described in J. A. Lewis and G. C. Papavizas, *Phytopathol.* 74:1240-1244 (1984); the contents of which are hereby incorporated by reference, and grown at about 4° C. for about 22 days. Radial growth of these isolates was measured and compared with the growth of sLTB, a fast growing snow mold fungi. Fifty six cold tolerant, rapidly growing Trichoderma isolates were obtained.

A dual culture method was employed to study the ability of Trichoderma to inhibit the growth of other fungi. In these mycoparasite studies, plugs of approximately 4 mm in diameter, taken from a culture of pathogenic fungi and from Trichoderma isolates, were placed opposite each other on the PDA plates and incubated at about 7° C. and at about 20° C. for about three weeks. Interactions between Trichoderma isolates and pathogenic fungi were observed. Isolates, designated CHS 861 (ATCC 74015), Biotype 603 (ATCC 74018), and Biotype 901 (ATCC 74017), were shown to parasitize *B. cinerea, R. solani*, Pythium spp., *S. borealis, F. nivale, T. incarnata, T. idahoensis, T. ishikariensis, V. dahliae, S. sclerotiorum, S. rolfsii*, and *S. cepivorum* as well as sLTB and *C. psychromobidus* (LTB) under laboratory conditions. Isolates, CHS 861 (ATCC 74015), Biotype 453 (ATCC 74016), Biotype 603

(ATCC 74018), and Biotype 901 (ATCC 74017), were also found to be effective in controlling the growth and development of *B. cinerea*, Pythium spp., *R. solani, S. borealis, F. nivale, T. incarnata, T. idahoensis, T. ishikariensis, V. dahliae, S. sclerotiorum, S. rolfsii, S. cepivorum* and sLTB. Isolate CHS 861 (ATCC 74015) was found to inhibit the growth and development of *A. mellea*. Isolate CHS 861 (ATCC 74015), Biotype 453

(ATCC 74016), Biotype 603 (ATCC 74018), and Biotype 901 (ATCC 74017) were found capable or promoting the growth, development and viability of non-infected plants, such as peas and flowering plants.

The colony characteristics, spore morphology, and branching patterns of the conidiophore of isolate CHS 861 (ATCC 74015) were examined. Isolate CHS 861

(ATCC 74015) is fast growing. At about 20° C. colonies reached 9 cm in diameter in 4 days when grown on oatmeal agar as described in Gooding and Lucas, *Phytopathol* 49:277–281 (1959), the contents of which are hereby incorporated by reference. This isolate also displayed marked tolerance to low temperatures. At 7° C. colonies reached 9 cm in diameter in 9 days on oatmeal agar. At about 4° C., CHS 861 (ATCC 74015) colonies grew slower, but the colonies were well established and their morphology appeared normal. The maximum growth temperature for this fungus was 33° C. (See FIG. 10). The pH range for the growth of isolate CHS 861 (ATCC 74015) extends from about pH 1.5 to about pH 10.0, with a growth optimum of from about pH 2.5 to about pH 5.5 (See FIG. 11).

The colonies of CHS 861 (ATCC 74015) were hyaline. They turn olive green to dark green in color after sporulation. Conidiophores were long and slender. They often were found to anastomose with each other which resulted in a compact hyphal network. Unlike the anastomosing sterile hyphal elongation found in *T. hamatum* and *T. polysporum*, anastomosis of CHS 861 was found in fertile conidiophores. Conidiophores of CHS 861 terminated in phialids, which are usually dispersed in numbers of 2 or more. The phialides were irregularly bent and were about 5.4–8.1×3.2–4.4 microns. Conidia (phialospores) were green in color and were globose to ovoid in shape. The mycelium was hyaline, smooth-walled, and septate with a size of about 2.7–5.4 microns. The size of the conidia ranged from about 2.4 microns to about 4.1 microns by about 2.4 microns to about 3.5 microns. This range in size of the conidia results in a length-width ratio of less than about 1.25. Light and scanning electron microscopy of three week old colonies showed that the surface of the conidia was very smooth and devoid of any ornamentations. Hyphae of CHS 861 form thick walled hyaline chlamydospores which mostly arise in an intercalary position. Colonies of CHS 861 (ATCC 74015) produced a very strong coconut odor on PDA, oatmeal agar, and V-8 juice agar media.

The spore ornamentation, spore size and shape, the length and whorl arrangement of phialids, the presence of anastomosis, and the coloration of the colonies of isolate CHS 861 (ATCC 74015) were compared to those of other Trichoderma species. Based upon these characteristics it was quite evident that isolate CHS 861 (ATCC 74015) differed from *T. hamatum, T. viride* and *T. harizanum* taxonomically.

Isolate CHS 861 (ATCC 74015) was found to be resistant to Terraclor (PCNB-pentachlornitro benzene) and Ridomil (N-[2,6-dimethylphenyl]-N-[methoxyacetyl]-alanine methyl ester), but was found to be highly sensitive to Benomyl. Its growth was found to be arrested completely at a Benomyl concentration of about 5 mg/ml.

Desirable Trichoderma mutants, e.g., pesticide resistant mutants, can be induced by conventional mutagenesis. In one embodiment of the present invention, isolate CHS 861 (ATCC 74015) was mutagenized by exposure to ultraviolet (UV) radiation to obtain Benomyl resistant Trichoderma mutants. Other Trichoderma mutants can be obtained by conventional techniques such as by choice of the appropriate selective medium. More specifically, the induction and isolation of Benomyl resistant mutants was accomplished in the following manner. Cultures of CHS 861 (ATCC 74015) [on PDA plates] at the active sporulation stage (3 days old culture grown at 20° C.) were placed under a GE Germicidal lamp, at a distance of approximately 22 cm. After UV irradiation, for a predetermined period of time, sterile distilled water in a volume of about 5 ml was pipetted onto the culture plates. Irradiated spores were detached gently from the conidiophore by a rubber policeman and cultured on V-8 juice agar supplemented with Benomyl at a concentration of about 100 mg/ ml or higher.

Colonies that grew on these plates were then transferred to V-8 juice agar plates without added Benomyl and incubated at 4° C. for 20 days. The rate of radial growth and sporulation, the spore morphology, and the capability of these mutants ("biotypes") to mycoparisitize were measured and compared with the wild type Trichoderma isolate CHS 861 (ATCC 74015). UV-induced Benomyl resistant biotypes were found that were highly resistant to Benomyl up to a concentration of about 1000 mg/ml.

These biotypes were morphologically indistinguishable from isolate CHS 861 (ATCC 74015), but some changes in their growth habits, antifungal capabilities, and their ability to promote the growth and development of plants were observed. The growth rate of the biotypes were slightly slower than that of the wild type. In a growth study conducted at about 4° C. for 20 days, the radial growth of Biotype 453 (ATCC 74016), Biotype 603 (ATCC 74018), and Biotype 901 (ATCC 74017) were about 59, 66, and 49 cm in diameter, respectively, compared to a radial growth of 70 cm for CHS 861 (ATCC 74015) under the same conditions.

The antifungal properties of Biotype 603 (ATCC 74018) were comparable to those of CHS 861 (ATCC 74015). However, a slight decrease in the antifungal properties of Biotype 453 (ATCC 74016) and Biotype 901 (ATCC 74017) respectively, as compared to those of CHS 861 (ATCC 74015) was observed when assayed on dual culture plates to determine the size of inhibition zones. Enhancement of plant growth and development was observed for all three biotypes. Pea seeds inoculated with Biotype 453 (ATCC 74016) produced the most vigorous plants as well as the earliest flowers.

No direct correlation was observed between the duration of UV radiation (15, 30, 45, 60, 90, 120, and 180 min.) and the number of Benomyl resistant biotypes induced.

In one embodiment of the present invention, the interaction of isolate CHS 861 (ATCC 74015) with selected soil-borne pathogens was studied. The mode of action appeared to vary. For instance, the clear zone of inhibition created by CHS 861 (ATCC 74015) on surrounding colonies was very pronounced in sLTB (approximately 6 mm. wide) and in *S. borealis*. This was not so evident in the case of *F. nivale*. However, a peculiar "bundled" mycelial formation was observed in *F. nivale*, but not with the other pathogens.

The zone of inhibition created by CHS 861 (ATCC 74015) and Biotype 603 (ATCC 74018) on *V. dahliae, S. Sclerotiorum, S. rolfsii*, and *S. cepivorum* were not evident. However, retardation of mycelial growth was observed on colonies of *V. dahliae, S. sclerotiorium, S. rolfsii, and S. cepivorum*. The results indicate that CHS 861 was very effective against all of these pathogens.

These results indicate that cold tolerant Trichoderma is effective against a wide range of plant pathogens indicating that cold tolerant Trichoderma is an effective general biocontrol agent against fungal plant disease.

The cold tolerant Trichoderma isolate and the Benomyl resistant mutants derived therefrom appear to be true mycoparasites. Both coiling and penetration of cold tolerant Trichoderma mycelia into the mycelia of the pathogenic fungi were observed in Pythium spp., *R. solani, C. psychromobidus*, Typhula spp., sLTB, *V. dahliae, S. sclerotiorium, S. rolfsii*, and *S. cepivorum.*

On the other hand, cold tolerant Trichoderma appeared to be able to forge a symbiotic relationship with plants. Mycelia and chlamydospore primordia of cold tolerant Trichoderma were observed in wheat cells with no adverse effects on the plants.

Mycelia "lysing" has been observed on colonies of sLTB and *B. cinerea* and *V. dahliae* when inoculated with a small clump of spores of isolate CHS 861 (ATCC 74015), Biotype 453 (ATCC 74016), Biotype 603 (ATCC 74018), and Biotype 901 (ATCC 74017). Penetration of isolate CHS 861 (ATCC 74015) Biotype 603 (ATCC 74018), Biotype 901 (ATCC 74017) hyphae into those of sLTB, LTB (*C. psychromobidus*), *V. dahliae*, Typhula spp., *R. solani*, and *F. nivale* and the perforation of the mycelia of these pathogenic fungi where associated with the Trichoderma isolate have been observed by light and scanning electron microscopy. Isolate CHS 861 (ATCC 74015) and Biotype 603 (ATCC 74018) were capable of inhibiting the development of microsclerotia of *V. dahliae*, and caused the rapid deterioration of conidia and microsclerotia that had previously formed.

In *S. borealis*, the sclerotia not only provides a means of survival for the snow mold fungus, but also serves as its primary source of inoculum. In light and scanning electron microscopic studies, Trichoderma isolate CHS 861 (ATCC 74015) has been found to be capable to parasitizing the sclerotia of *S. borealis* and using it as a food source. Penetration of the sclerotia of *S. borealis* by the mycelia of Trichoderma was found mostly through the nicks and cracks occurring in the rind. A mycelial "lysis" similar to that observed in sLTB has been observed on the medulla cells of *S. borealis.* The lysing of the large, thin-walled medulla cells resulted in the rapid loss of the integrity of the medulla. The sclerotia then became cavernous and hollow-centered. The sclerotia is able to support the growth and development of Trichoderma. Sporulation of the Trichoderma isolates have been observed both on the exterior and interior of the diseased sclerotia.

In order to understand whether the "lysing" of the snow mold fungal mycelia by cold tolerant Trichoderma is a result of a chemical action, the snow mold fungus was cultured in the presence of culture filtrates of Trichoderma. The experiment results indicated that the crude culture filtrates significantly reduced the radial growth of sLTB, Pythium spp., *V. dahliae, S. sclerotiorum*, and *S. rolfsii.* Two molecules were identified from the culture filtrates and found to possess inhibitory effects on the growth of sLTB. The estimated molecular weights of these molecules, by the gel filtration method, were found to be 17,000 Da and 21,000 Da respectively. These molecules were fractionated through a fine grade, Sephadex 75 column calibrated with Bio-Rad protein standards (Bio-Rad Laboratories) and were measured at 280 nm using an Elmer-Parker spectrophotometer. Both of these molecules, which are proteinaceous in nature, were found to be heat stable.

In order to verify that the 17 kDa and 21 kDa molecules are proteins, the purified preparations were incubated with pronase. The proteolyzed material was assayed by their ability to inhibit growth of sLTB and was found to be entirely degraded and is no longer biologically active. This result indicates that the 17 and 21 kDa molecules are sensitive to proteases and are proteins.

The culture filtrates were further analyzed for lower molecular weight material by ultrafiltration in an Amicon 8050 ultrafiltration device. The crude culture filtrate was filtered through an Amicon filter with a molecular weight cut-off of 5,000. The material retained by the filter was filtered through a second Amicon filter with a molecular weight cut-off of 10,000. A third molecule was identified within the material that passed through the second filter. This third molecule was found to possess inhibitory effects on the growth of sLTB and was further characterized. This molecule was found to be sensitive to pronase at a concentration of 0.1 mg/1. This 5-10 kDa molecule is purified by gel-filtration chromatography, ion exchange chromatography, affinity chromatography and HPLC. This molecule was also found to exhibit antibacterial activity such as against *Clavibacter sepidonicum.*

In another embodiment of the present invention, the cold tolerant Trichoderma isolate and the Benomyl resistant biotypes were used to protect winter wheat plants against fungal disease, such as snow mold disease. For example, winter wheat seedlings, germinated from seeds coated with spores of cold temperature Trichoderma were inoculated with sLTB, and incubated at about 4° C. for about 8 weeks. A significant increase of winter wheat survival was observed on seedlings treated with the cold tolerant Trichoderma isolate. Examination of the sheath of Trichoderma treated winter wheat also revealed a dramatic reduction in the number of sclerotia formed by sLTB.

In a further embodiment of the present invention, cold-tolerant Trichoderma was used to protect plants against damping off disease. For example, under greenhouse conditions, garden peas were coated with Trichoderma spores and planted in Pythium spp. infested soils. The Pythium isolates that were tested are *P. aphanidermatum, P. dissotocum, P. oligandrum, P. ultimum*, as well as a species isolated from chrysanthemum seedlings obtained from a commercial greenhouse. Significant differences were found as to germination and survival of peas between those treated with cold tolerant Trichoderma and the unprotected controls.

In as yet another embodiment of the present invention, cold tolerant Trichoderma was used to promote growth of plants in the absence of detectable pathogens. For example, in experiments on the effect of cold tolerant Trichoderma on the growth and development of garden peas, significant increases in weight, height, as well as the numbers of flowers and fruits were found in Trichoderma treated pea plants compared to untreated controls. Other vegetables and flowers have been tested and qualitatively similar results have been obtained.

Viability of biological control agents in soil is one of the central issues regarding field applications. Preliminary tests on the survival of isolate CHS 861 (ATCC 74015) through the Alaskan winter were conducted. In the Fall, isolate CHS 861 (ATCC 74015) colonized rye kernels were buried in the soil at the root zone of wheat plants. After Spring break-up, isolate CHS 861 (ATCC 74015) was reisolated from the rye kernels after excavation. Results of the viability tests indicated that isolate CHS 861 (ATCC 74015) can survive well in the soil through six months of winter conditions.

There are a variety of possible ways of applying the cold tolerant Trichoderma CHS 861 (ATCC 74015), Biotype 453 (ATCC 74016), Biotype 603 (ATCC 74018), and Biotype 901 (ATCC 74017) to produce agricultural control and treatment of plant diseases and promotion of plant growth. Conidia, mycelia, or chlamydospores of these mycoparasites can be applied directly to the soil, the plant or plant tissue, either alone or in combination. Direct application of the mycoparasites is less effective, because the thin walled conidia and fungal mycelia can quickly lose their viability due to desiccation.

Addition of a carrier comprising agriculturally acceptable inert substances such as that sold under the trade name Pyrax by R. T. Vanderbilt Co., Inc. (CT, USA), as well as alginate-Pyrax, clay, koalin, and peat moss, etc., can improve the effectiveness of the treatments markedly. Adjuvants such as emulsifiers, sticking agents, suspending agents, etc., may also be used to improve the adhesiveness of the mycoparasites and further enhance the antifungal activities of the isolate.

Trichoderma compositions can be applied in a solid or liquid form. The solid form includes dust, wettable powder, granules, and pellets. The liquid compositions may be in the form of an aqueous or non-aqueous media, in solution, suspension, dispersion, or concentrated form. The cold tolerant Trichoderma compositions may also contain another pesticide or chemical agent. The added pesticide may be a chemical pesticide such as Terraclor, Ridomil, or Benomyl to which either CHS 861 (ATCC 74015) or its mutants are resistant. This pesticide may also be another biocontrol agent such as a bacterial mycoparisite (for example, *Pseudomonas fluorescens*), or a different species or isolate of Trichoderma.

The preferred concentration of conidia, mycelia, or chlamydospores of cold tolerant Trichoderma in a carrier is from about $10^5$ to about $10^8$ colony forming unit (cfu)/gram of solid composition or about $10^5$ to about $10^8$ cfu/gram of liquid composition.

The Trichoderma composition can be applied in the field for the purpose of soil treatment or reestablishment of microorganisms after soil-fumigation or heat treatment. The amount that is used can be from about 50 grams to about 100 grams (dry weight) per square meter of soil. In the greenhouse, the biocontrol composition can be applied at approximately 5 grams per kg. of potting mix.

In another embodiment of the present invention, the Trichoderma composition was applied to seeds as a coating. In a preferred embodiment, alginate-Pyrax was used as a carrier for the encapsulation of seeds of, for example, winter wheat and pea with cold tolerant *Trichoderma mycelia* and spores. In another embodiment a Trichoderma composition further containing an agriculturally acceptable adhesive, for example, that sold under the trade name Pelgel by Nitragin (WI, USA), can be applied to seeds as a coating for purposes of protecting plants against fungal diseases such as damping off, black scurf, snow mold, and root rot. A Trichoderma composition containing adhesive can also be applied to seedlings and fruits, for example, grapes and strawberries, in order to protect them from grey mold caused by *B. cinerea.*

By way of example the Trichoderma composition may be applied to the seeds as follows. A Trichoderma spore suspension is added to a 1% sodium alginate solution (obtained from Sigma Chemical Co., St. Louis Mo.) to a concentration of about 2.0×105–20×106 spores/ml. The seeds to be coated are added to the sodium alginate spore suspension. The coated seeds are individually taken from the sodium alginate spore suspension and placed into a 50 mM CaCl2 solution for several minutes. The coated seeds are then dried on paper towels in a laminar flow hood.

Molecules in Trichoderma culture filtrates can be applied to produce agricultural control and treatment of plant diseases and promotion of plant growth. The molecules can be applied in a biologically pure form or in combination with other molecules, including agriculturally suitable carriers. In other embodiments of the invention, an agriculturally effective amount of a filtrate comprised of Trichoderma culture medium containing these molecules or a Trichoderma culture medium containing these molecules and substantially free of viable Trichoderma microorganisms can be applied to the plant to be treated or protected.

The following examples are given by way of illustration to facilitate a better understanding of the invention and are not intended to limit the invention. It should be further understood that the detailed description while indicating preferred embodiments of the invention, is given by way of illustration only, since various changes and modifications within the spirit and scope of the invention will become apparent to those skilled in the art from the detailed description.

EXAMPLE 1

Cold tolerant Trichoderma CHS 861 (ATCC 74015) and Biotype 603 (ATCC 74018) were cultured on PDA plates at 20° C. under continuous lighting for 7 days. Conidia produced in the cultures were washed off by using a wash bottle of cold distilled water and were collected in a container. A small aliquot of the conidia suspension was removed and diluted for counting in an AO Spencer Bright-line Hemacytometer.

For seed encapsulation, 5 g of sodium alginate plus 50 g of Pyrax ABB were mixed into 500 ml of distilled water in a Waring blender for 1 minute. The spore suspension was added to the alginate-Pyrax mixture to produce a final spore concentration of $2\times10^5$ spores/ml. Pea seeds were added to the spore-alginate-Pyrax suspension and mixed thoroughly. These pea seeds were then dropped into a calcium gluconate solution, prepared by dissolving 21.5 g of calcium gluconate in 1 liter of distilled water.

Encapsulated pea seeds were collected, dried and planted in perlite inoculated with Pythium spp. at $10^3$ sporangia/g of soil. Significant increases in the germination of pea seeds was observed in those treated with CHS 861 (ATCC 74015) (66% germination) or Biotype 603 (ATCC 74018) (44% germination) when compared to the seeds without Trichoderma treatment (11% germination). The results are shown in FIG. 1. A slight decline in germination was found in Biotype 603 (ATCC 74018) treated seeds. No adverse effect on the germination of pea seeds was found when they were treated with Trichoderma CHS 861 (ATCC 74015).

A statistical analysis of the data was performed using the Duncan multiple range test as described in *Sokal* et al., Biometry, Freeman Pbl. Co., 1969, which is hereby incorporated herein by reference. Identical letters above the mean for each data point indicate no statistically significant differences between such data points.

EXAMPLE 2

Figure 2:
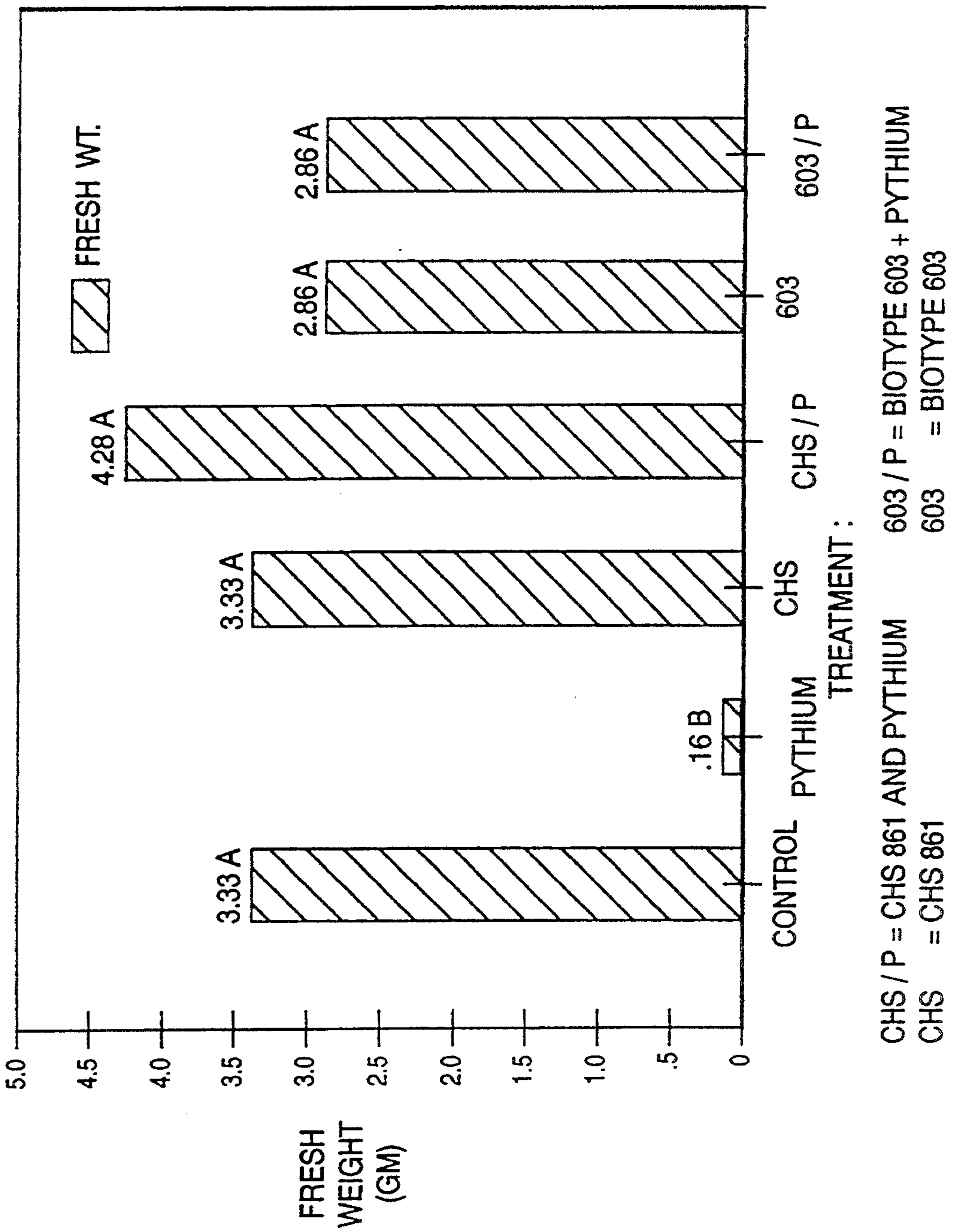
FIG. 2: A comparison of the effect of Trichoderma isolate CHS 861 (ATCC 74015) and its mutant, Biotype 603 (ATCC 74018), on the fresh weight of peas inoculated with Pythium spp.

After germination, the pea plants were allowed to grow for two weeks and then were harvested. The ability of the plants to survive and grow, measured in terms of fresh weight was determined. Untreated pea plants, when grown in Pythium spp. treated soil, showed very poor growth, as shown in FIG. 2. There was a significant increase in the fresh weight of pea plants germinated from CHS 861 (ATCC 74015) and Biotype 603 (ATCC 74018) treated seeds in infected soils. No statistical differences were found among the fresh weights of plants germinated from CHS 861 (ATCC 74015) or Biotype 603 (ATCC 74018) treated seeds when compared to an untreated control. No statistical differences were found on the fresh weight of pea plants germinated from CHS 861 (ATCC 74015) or Biotype 603 (ATCC 74018) treated seeds grown in soils with or without Pythium infestation.

EXAMPLE 3

Figure 3:
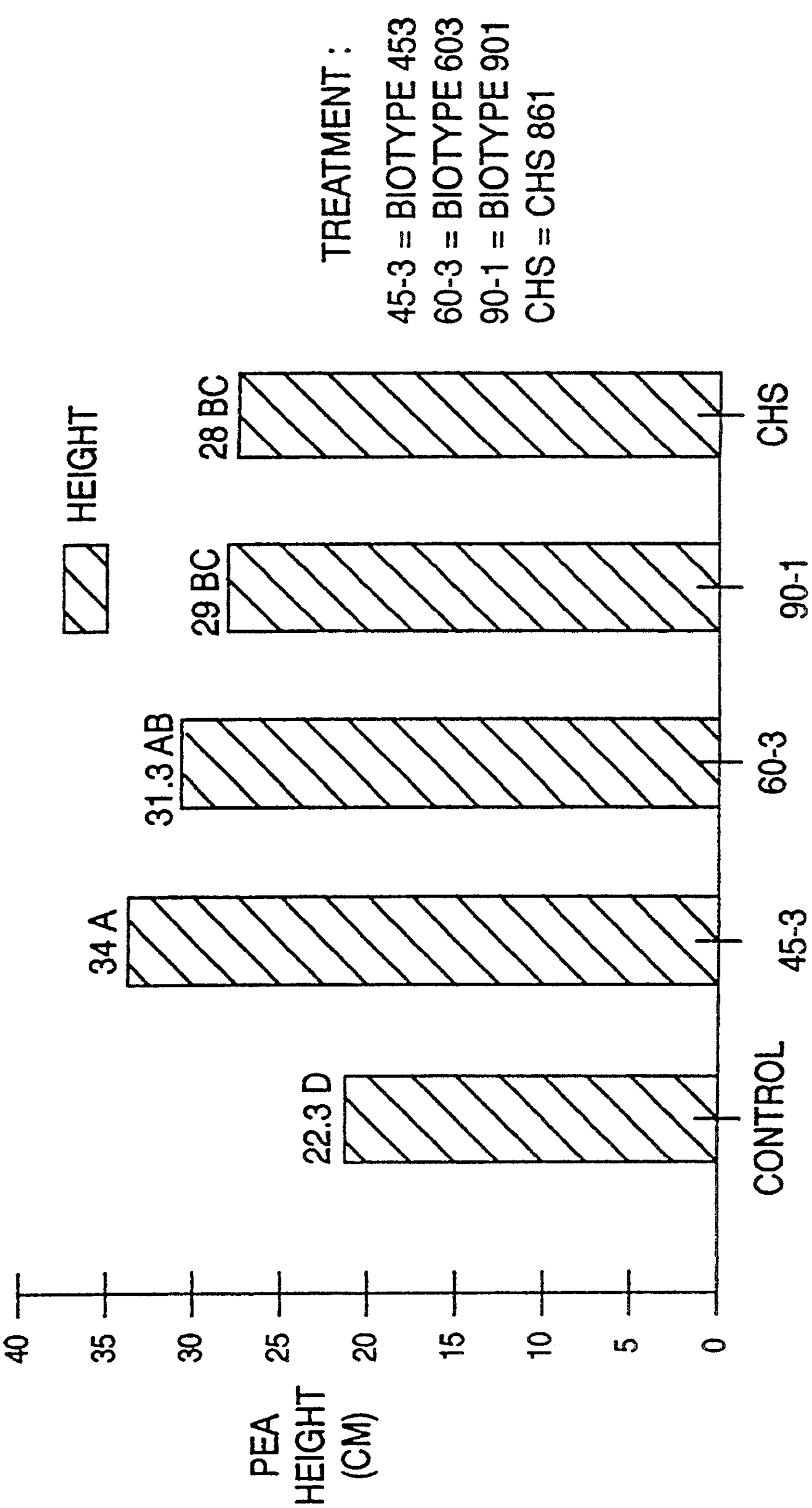
FIG. 3: A comparison of the effect of the Trichoderma isolate and its mutants on pea plant height.

The effect of cold tolerant Trichoderma CHS 861 (ATCC 74015), Biotype 453 (ATCC 74016), Biotype 603 (ATCC 74018), and Biotype 901 (ATCC 74017), respectively, on the growth and development of plants were examined in various ways. Garden pea seeds were coated with CHS 861 (ATCC 74015), Biotype 453 (ATCC 74016), Biotype 603 (ATCC 74018), or, Biotype 901 (ATCC 74017) in accordance with the method as described in Example 1. The coated seeds were germinated and grown in perlite without infestation of soilborne plant pathogens. After 4 weeks, the pea plants were harvested. The responses of the pea plants to treatments, expressed in terms of pea height are shown in FIG. 3. Biotype 453 (ATCC 74016) treated plants were significantly taller than all other treatments. Pea plants treated with CHS 861 (ATCC 74015) and the three indicated biotypes were significantly taller than the control.

EXAMPLE 4

Figure 4:
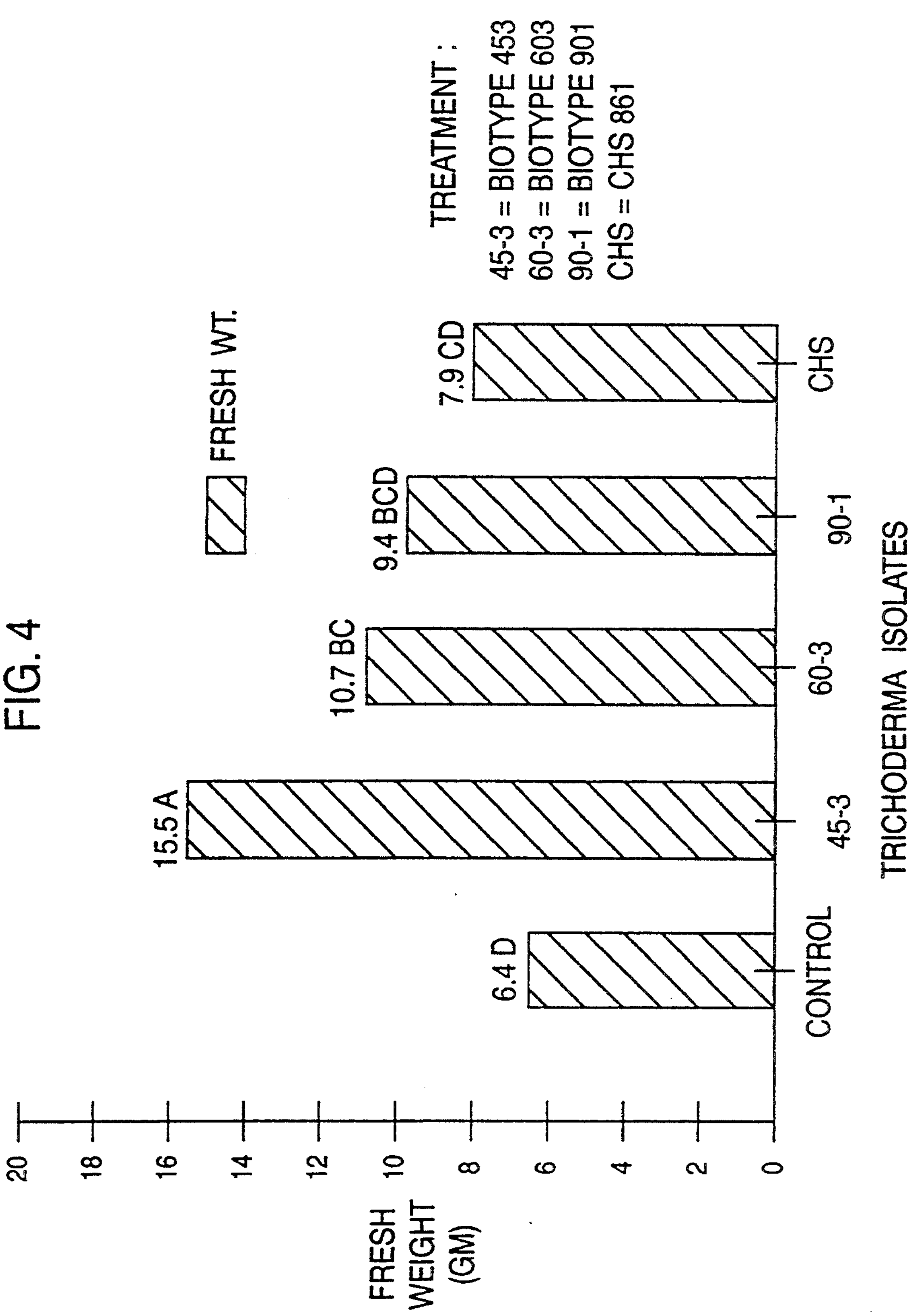
FIG. 4: A comparison of the effect of the Trichoderma isolate and its mutants on pea fresh weight.

Responses of pea plants to treatment, (as described in Example 3), of cold tolerant Trichoderma CHS 861 (ATCC 74015), Biotype 453 (ATCC 74016), Biotype 603 (ATCC 74018), and Biotype 901 (ATCC 74017), measured in terms of as fresh weight, are shown in FIG. 4. Biotype 453 (ATCC 74016) treated plants were significantly heavier than all other treatments. Pea plants treated with CHS 861 (ATCC 74015) and the three biotypes were all significantly heavier than the control.

EXAMPLE 5

Figure 5:
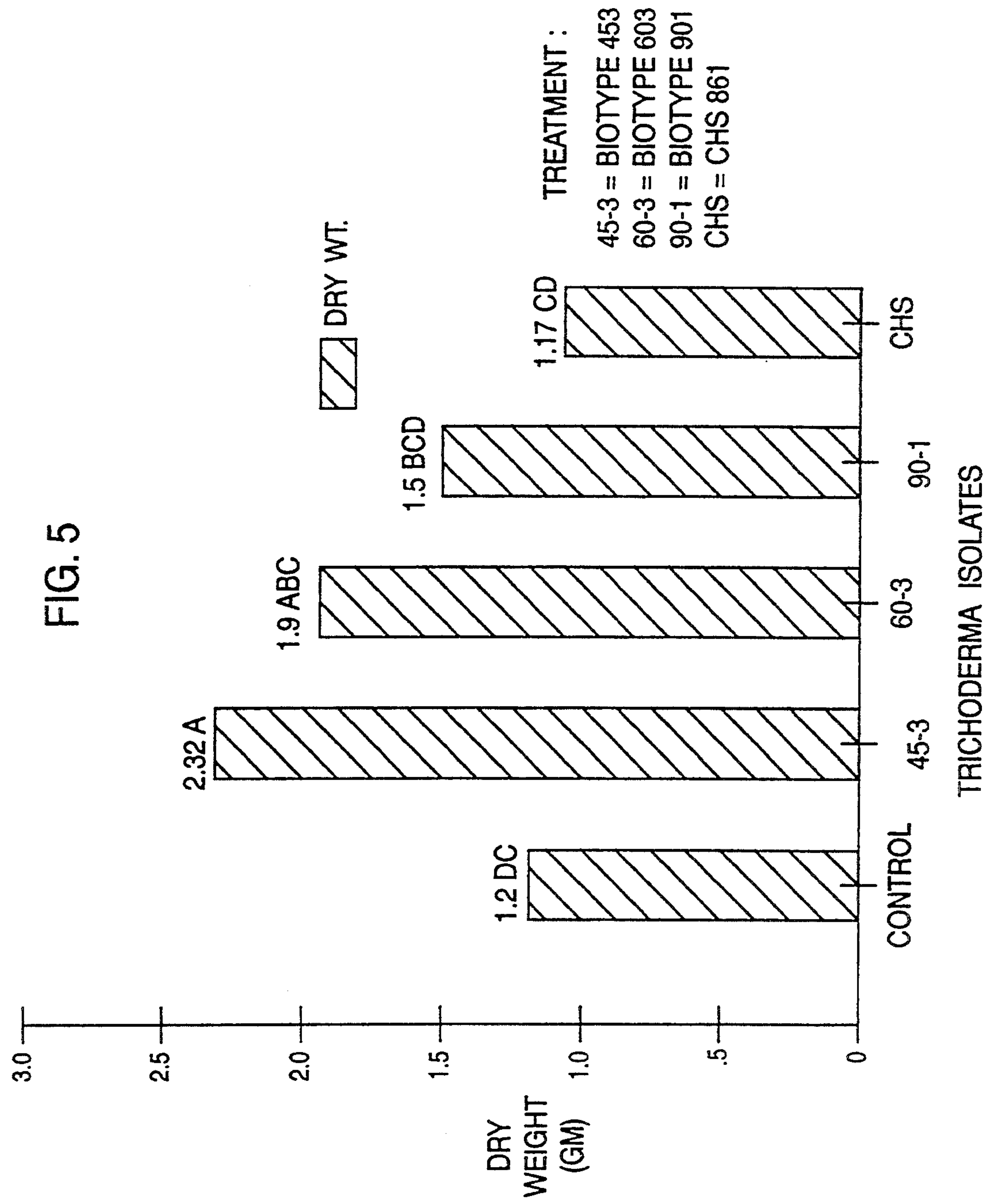
FIG. 5: A comparison of the effect of the Trichoderma isolate and its mutants on pea dry weight.

Responses of pea plants to treatment, (as described in Example 3), of cold tolerant Trichoderma CHS 861 (ATCC 74015), Biotype 453 (ATCC 74016), Biotype 603 (ATCC 74018), and Biotype 901 (ATCC 74017), measured in terms of dry weight, are shown in FIG. 5. Biotype 453 (ATCC 74016) treated plants produce significantly more solid mass than the control. Although a slight decrease of dry weight was observed on peas treated with CHS 861 (ATCC 74015), pea plants treated with the 3 biotypes produce significantly more mass than the control.

EXAMPLE 6

Figure 6:
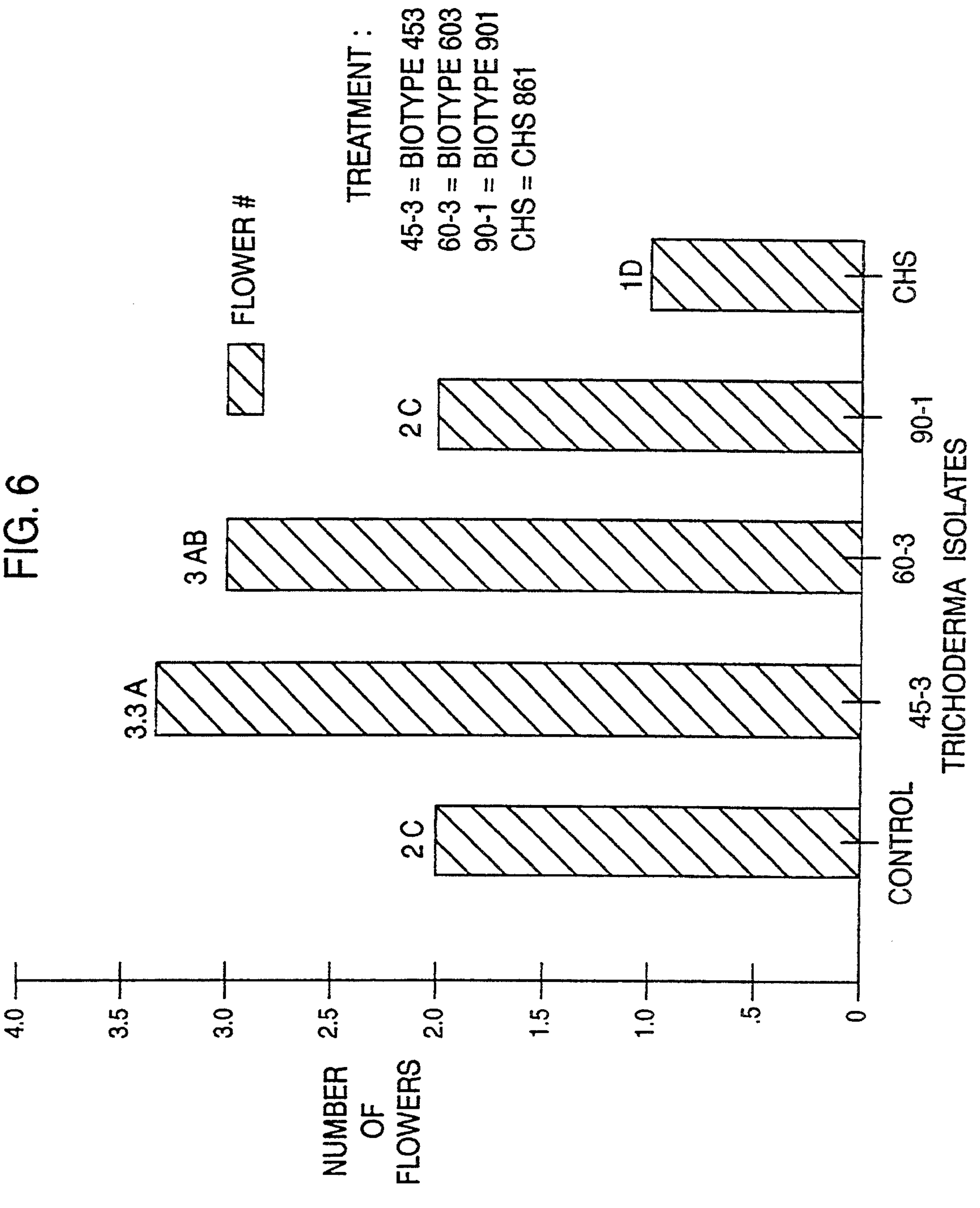
FIG. 6: A comparison of the effect of the Trichoderma isolate and its mutants on flower production.

Responses of pea plants to treatment, (as described in Example 3), of cold tolerant Trichoderma CHS 861 (ATCC 74015), Biotype 453 (ATCC 74016), Biotype 603 (ATCC 74018), and Biotype 901 (ATCC 74017), measured by flower production, are shown in FIG. 6. Biotype 453 (ATCC 74016) treated plants flowered earlier and produce significantly more flowers than the untreated control.

EXAMPLE 7

The effect of cold tolerant Trichoderma culture filtrates on the growth and development of pathogenic fungi was studied as follows. Trichoderma CHS 861 (ATCC 74015) was grown in 50 ml of Glucose Yeast Extract (GYE) liquid medium as described in Madelin, M. F., Ann. Bot. 20:307-330 (1956) for 10 days at 10° C. The cultures were then blended for 15 seconds in a Waring blender and were filtered through 4 layers of cheesecloth. This was followed by filtration through Whatman No. 1 filter paper under vacuum. The filtrate was then centrifuged at 10,000 rpm (12,350 g) for 15 minutes. The supernatant was collected, concentrated 20-fold with a rotary evaporator, and filtered through a sterile 22 micron millipore filter.

Figure 7:
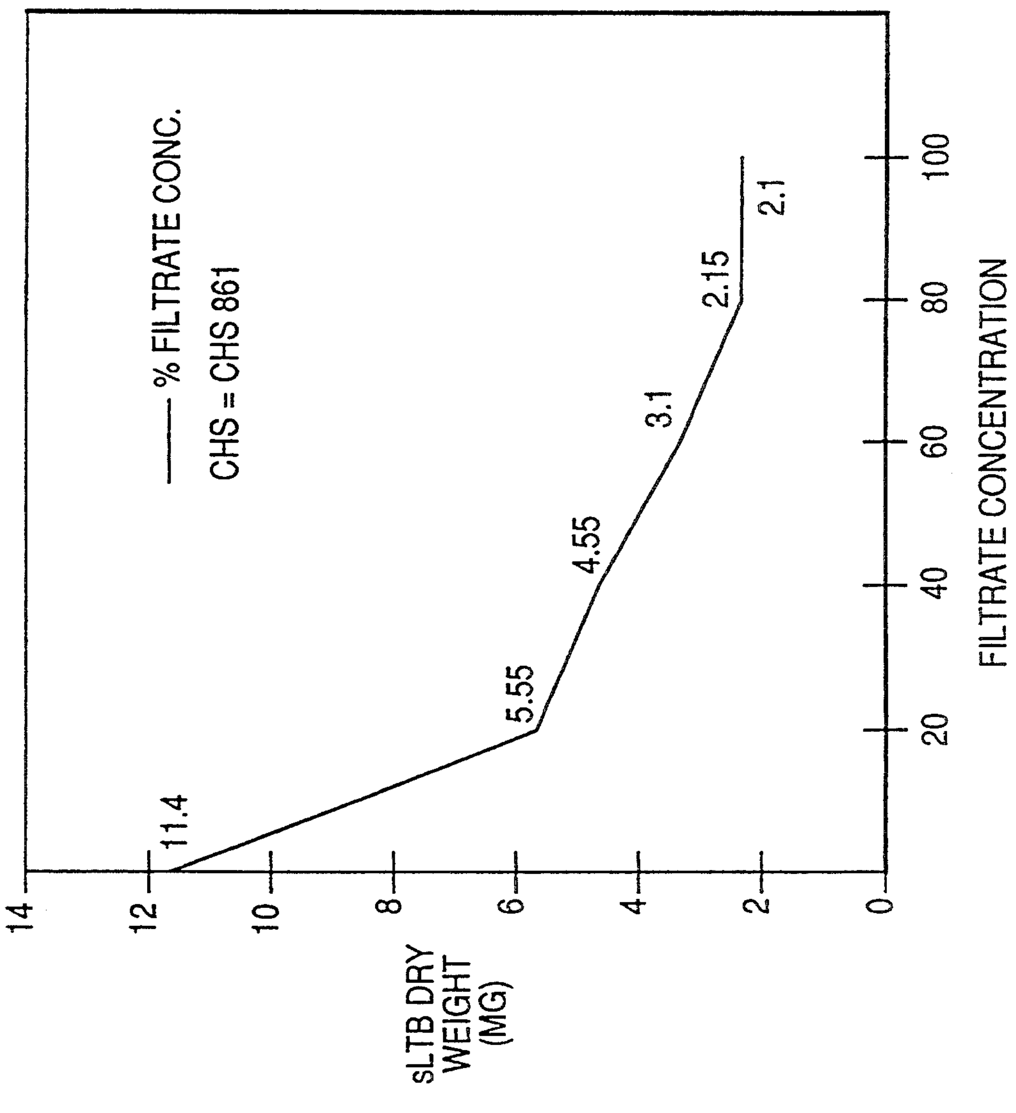
FIG. 7: Effect of CHS 861 (ATCC 74015) filtrate on sLTB dry weight.

Dilutions were made of this concentrated culture filtrate preparation in 20 ml. of GYE liquid media. Five plugs, 1 cm in diameter each, of sLTB were placed in each culture filtrate containing flask and allowed to incubate in the media for 2 weeks at 10° C. Mycelia of sLTB on the agar plugs were harvested onto overdried preweighed paper under vacuum. The mycelia were oven dried and weighed. The culture filtrate of CHS 861 (ATCC 74015) was found to significantly inhibit the growth and development of sLTB. The antimycotic activity of the culture filtrate corresponded directly with the concentration of the filtrate. The results are shown in FIG. 7.

EXAMPLE 8

In studying the stability of the antimycotic activity in the culture filtrate of the cold tolerant Trichoderma, the culture filtrate of CHS 861 (ATCC 74015) was prepared according to the method described in Example 7, omitting the concentration process. Dilutions of the filtrate were made and added to GYE agar media after the filtrate were either filter-sterilized or autoclaved. A sLTB plug of about 4 mm in diameter was placed in the center of a small plate with a designated culture filtrate and was incubated at 10° C. for 2 weeks.

Figure 8:
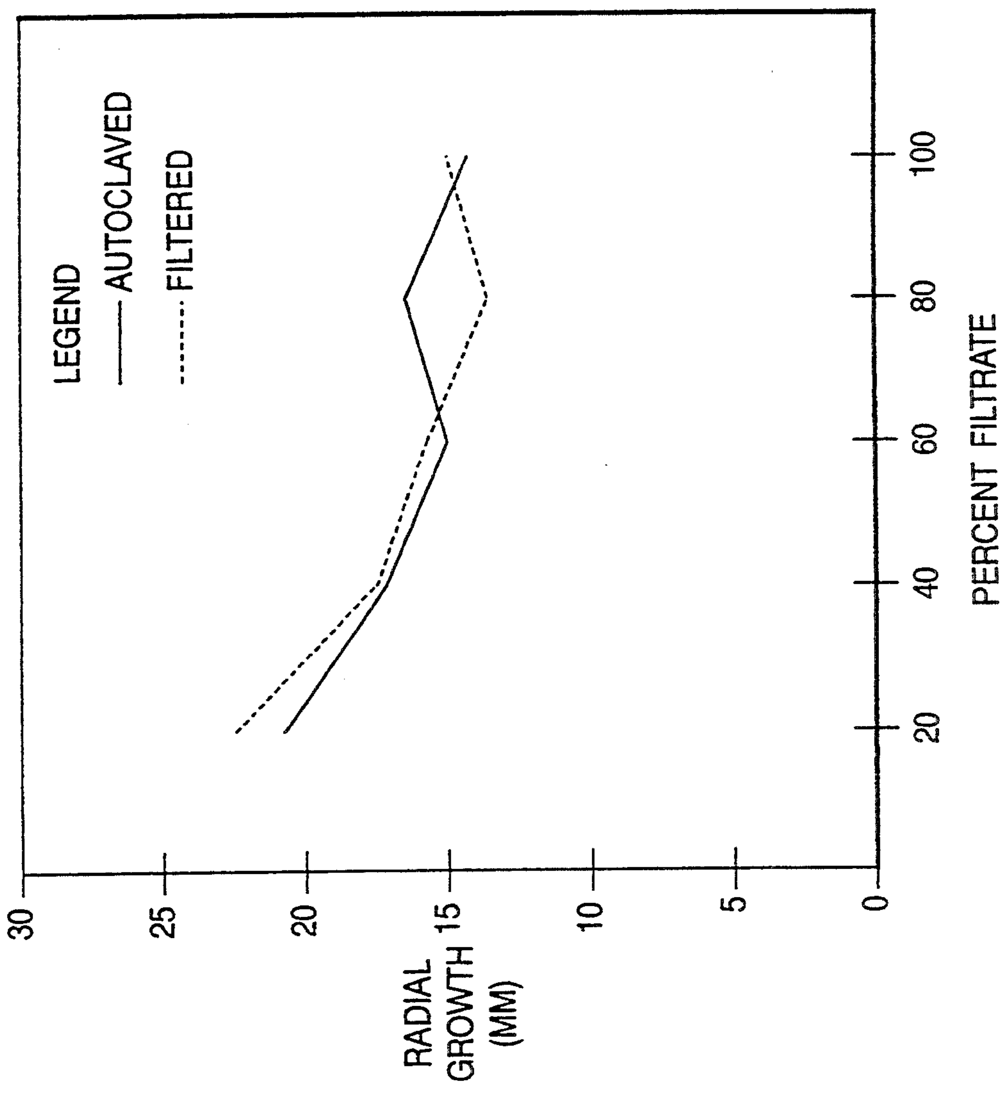
FIG. 8: A comparison of the effect of autoclaved and filter sterilized CHS 861 (ATCC 74015) filtrate on the radial growth of sLTB.

Radial growth of sLTB in the presence of culture filtrate was measured as the average of two transverse measurements. No significant difference was observed in antimycotic activity between the filter sterilized and autoclaved culture filtrates. The substances having antimycotic activity produced by cold-tolerant Trichoderma in liquid culture is not sensitive to heat treatment, as shown in FIG. 8.

EXAMPLE 9

Figure 9:
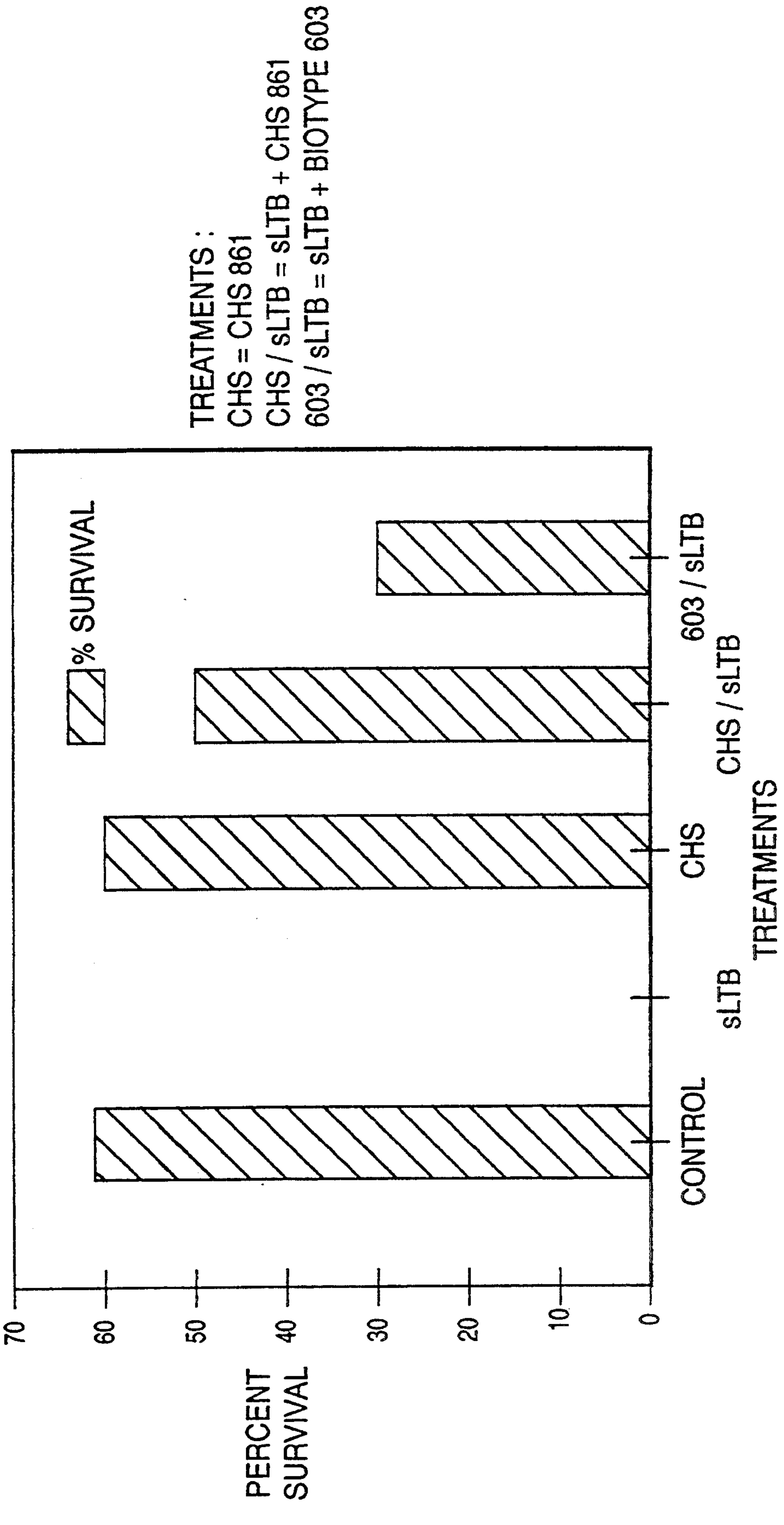
FIG. 9: A comparison of the effect of the Trichoderma isolate and its mutant on the survival of sLTB winter wheat.

The ability of cold tolerant Trichoderma and Biotype 603 (ATCC 74018) to protect plants against snow mold disease was studied. Winter wheat seeds, coated with CHS 861 (ATCC 74015) or Biotype 603 (ATCC 74018) according to the method described in Example 1, were germinated and grown to the 3-leaf stage. Wheat seedlings were then exposed to the snow mold fungus by piling sLTB colonized rye kernels around the base of the plant. Plants subjected to the treatments shown in FIG. 9 were placed in a cold (about 4° C.), dark, and moist (about 100% relative humidity) environment for 8 weeks. The results of the winter wheat survival study are shown in FIG. 9. Because of the extremely trying conditions, a certain degree of mortality was observed in all treatments including the control with no exposure to sLTB or mycoparasites. No survivors were found when winter wheat seedlings were treated with sLTB. A significant improvement in viability of winter wheat seedlings was observed when the seedlings were previously protected with Biotype 603 (ATCC 74018) or CHS 861 (ATCC 74015). A slight increase in mortality was observed in infected plants treated with Biotype 603 (ATCC 74018), as compared to infected plants treated with CHS 861 (ATCC 74015), but no difference was observed between infected plants treated with CHS 861 (ATCC 74015) and the control (no exposure to sLTB).

EXAMPLE 10

The temperature range of cold-tolerant Trichoderma was studied. Colonies of cold-tolerant Trichoderma (ATCC 74015) were innoculated on oatmeal agar. Oatmeal agar is comprised of 60 g rolled oats and 12 g of agar in 1 l of distilled water. The time required for the colonies to reach 9 cm. in diameter was measured when the colonies were incubated at various temperatures. The results are shown in FIG. 10.

EXAMPLE 11

Figure 11:
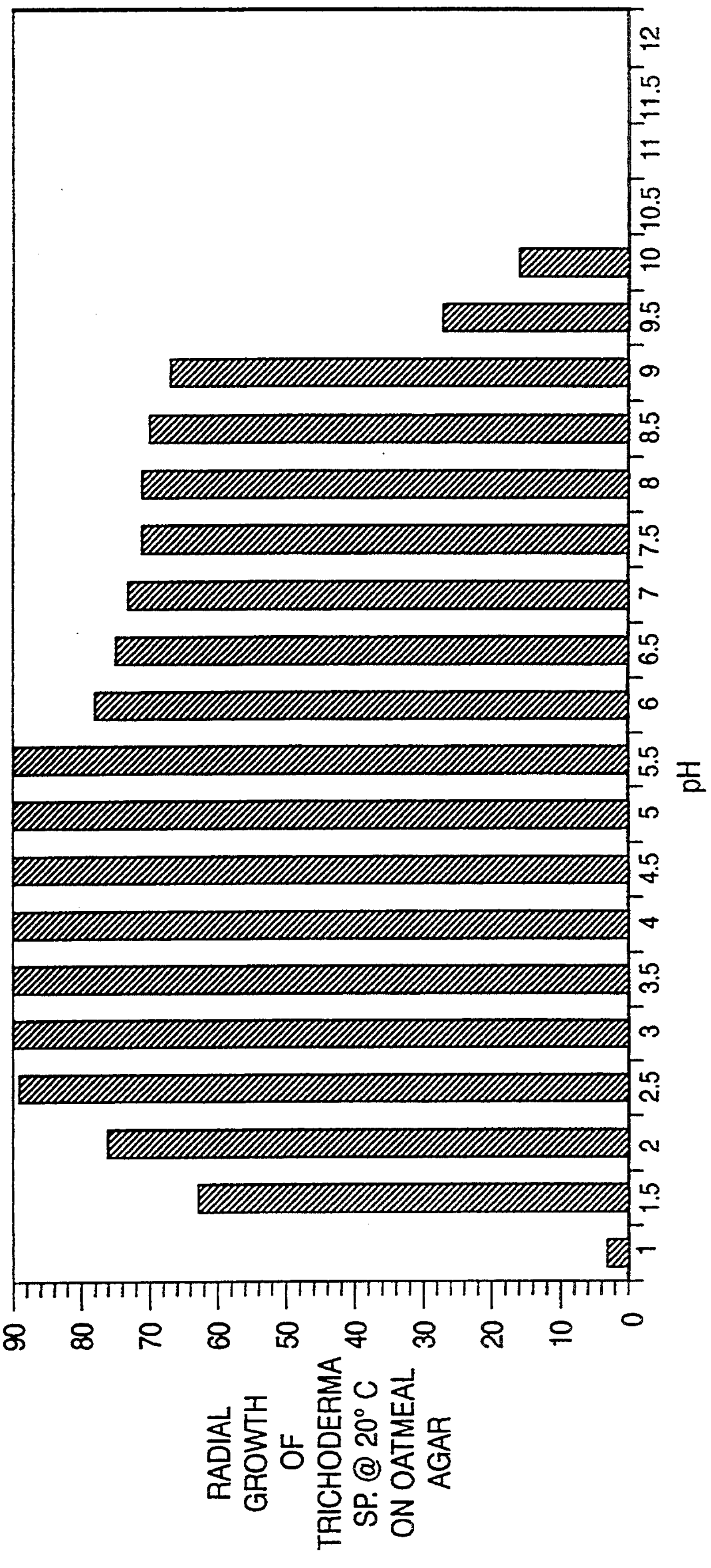
FIG. 11: A comparison of the effect of pH on the growth of cold tolerant Trichoderma (ATCC 74015).

The pH range of cold-tolerant Trichoderma was measured. Colonies of cold-tolerant Trichoderma (ATCC 74015) were innoculated on oatmeal agar and radial growth in mm after 7 days was measured as a function of pH. The results are shown in FIG. 11.

EXAMPLE 12

Three methods were employed to investigate the effects of cold-tolerant Trichoderma on the growth and development of *Verticillium dahliae*, *Sclerotinia sclerotiorium*, *Sclerotium rolfsii* and *Sclerotium cepivorum*. In the dual culture method, plugs of approximately 4 mm in diameter, taken from cultures of these pathogenic fungi, and from isolates CHS 861 (ATCC 74015) and Biotype 603 (ATCC 74018), were placed opposite each other on PDA plates and incubated at about 10° C. and 23° C. The growth and development of these pathogenic fungi were arrested totally in approximately 4 and 7 days when incubated at 23° C. and 10° C., respectively. In the case of *V. dahliae*, rapid deterioration of conidia (spores), and mycelia was observed in 7 days, when incubated at 23° C. No microsclerotia were ever formed.

In the seeding study, clumps of Biotype 603 (ATCC 74018) conidia were seeded on well-established *V. dahliae* with microsclerotia at various stages of development. Biotype 603 (ATCC 74018) was found to be able to arrest the development of new microsclerotia, and cause the deterioration of those already formed. Dead microsclerotia is hyaline rather than dark-colored.

In the culture filtrate method, plugs of *V. dahliae*, *S. sclerotiorum*, *S. rolfsii* and *S. cepivorum* were placed on PDA plates coated with a thin layer of culture filtrate. The culture filtrate was obtained by filtering a 10-day old culture through a 0.45 μm filter. No growth of *V. dahliae*, *S. sclerotiorium* and *S. rolfsii* was observed when they were placed on PDA plates coated with 1 ml of the culture filtrate of Biotype 603 (ATCC 74018).

Results of these studies indicated that both CHS 861 (ATCC 74015) and Biotype 603 (ATCC 74018) are excellent bio-control agents of *V. dahliae*, *S. sclerotiorum* and *S. rolfsii*, and good bio-control agents of *S. cepivorum*.

*Verticillium dahliae* causes wilt on many important crops and fruit and nut trees, e.g. cotton, potatoes, tomatoes, strawberries, crucifers, almonds, apples, apricots, cherries, nectarines, olives, peaches, pears, pistachio, persimmons, plums, prunes, walnuts, etc. *V. dahliae* is a slow-growing fungus but it is an extremely prolific producer of conidia and microsclerotia which often cause blockage in the water conducting vessels of plants and result in wilt and death of host plants. The ability of cold tolerant Trichoderma in causing rapid deterioration of *V. dahliae* conidia and microsclerotia could relieve the blockage and restore the vigor of plants.

EXAMPLE 13

The effect of cold-tolerant Trichoderma on the structural integrity of pathogenic fungi has been investigated.

Figure 12:
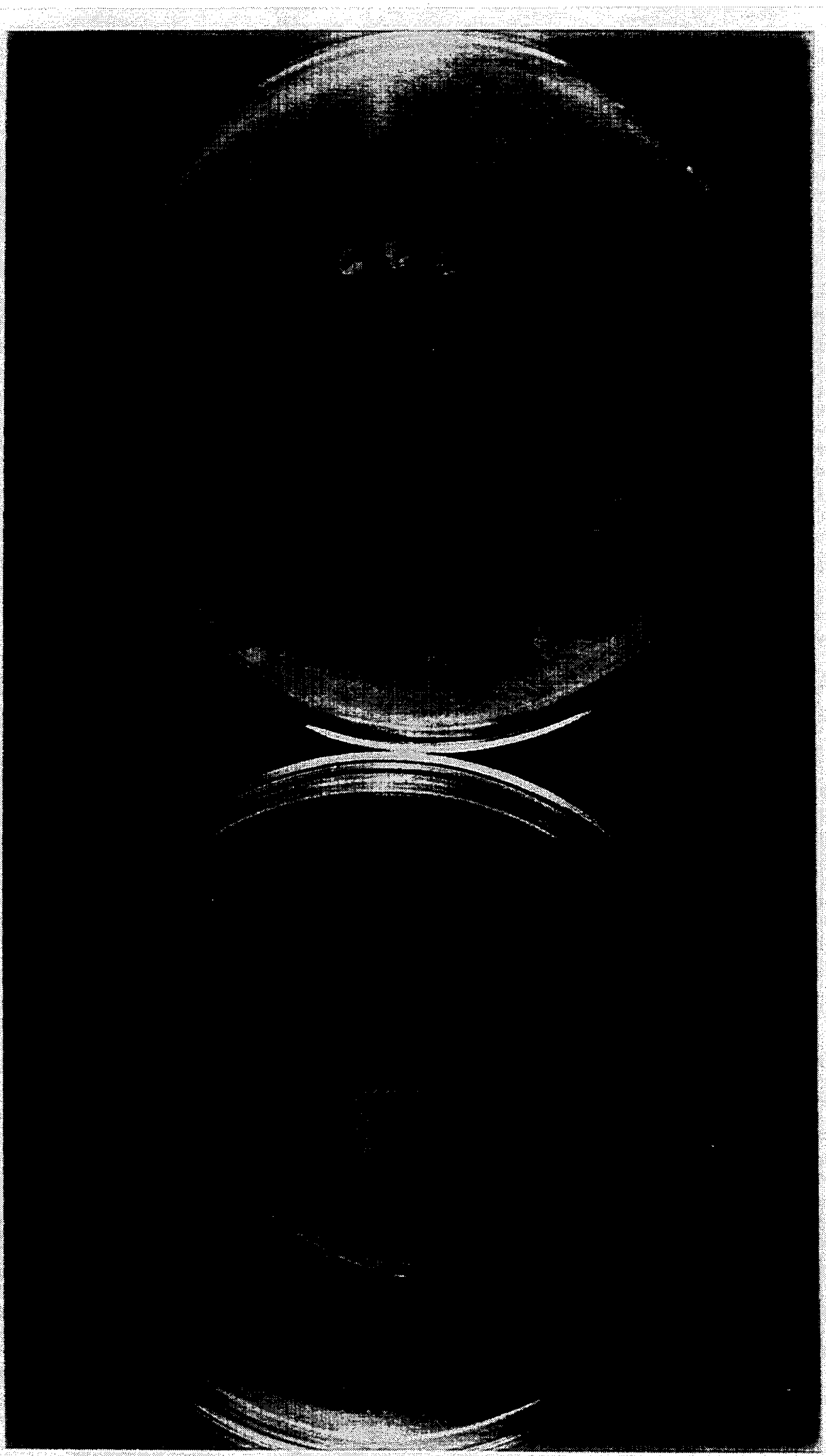
FIG. 12: A comparison of the outward appearance of a normal *V. dahliae* colony and a *V. dahliae* colony that has been parasitized by cold tolerant Trichoderma.

In a first series of experiments the effect of cold tolerant Trichoderma on the overall structure and morphology of *V. dahliae* colonies was investigated. In FIG. 12, the colony on the left is of healthy uninfected *V. dahliae*. The colony on the right is of *V. dahliae* that has been infected with CHS 861. The pathogenic effect of CHS 861 on *V. dahliae* is clearly visible to the naked eye in the colony on the right as indicated by loss of dark appearance vs. the untreated control.

Figure 13:
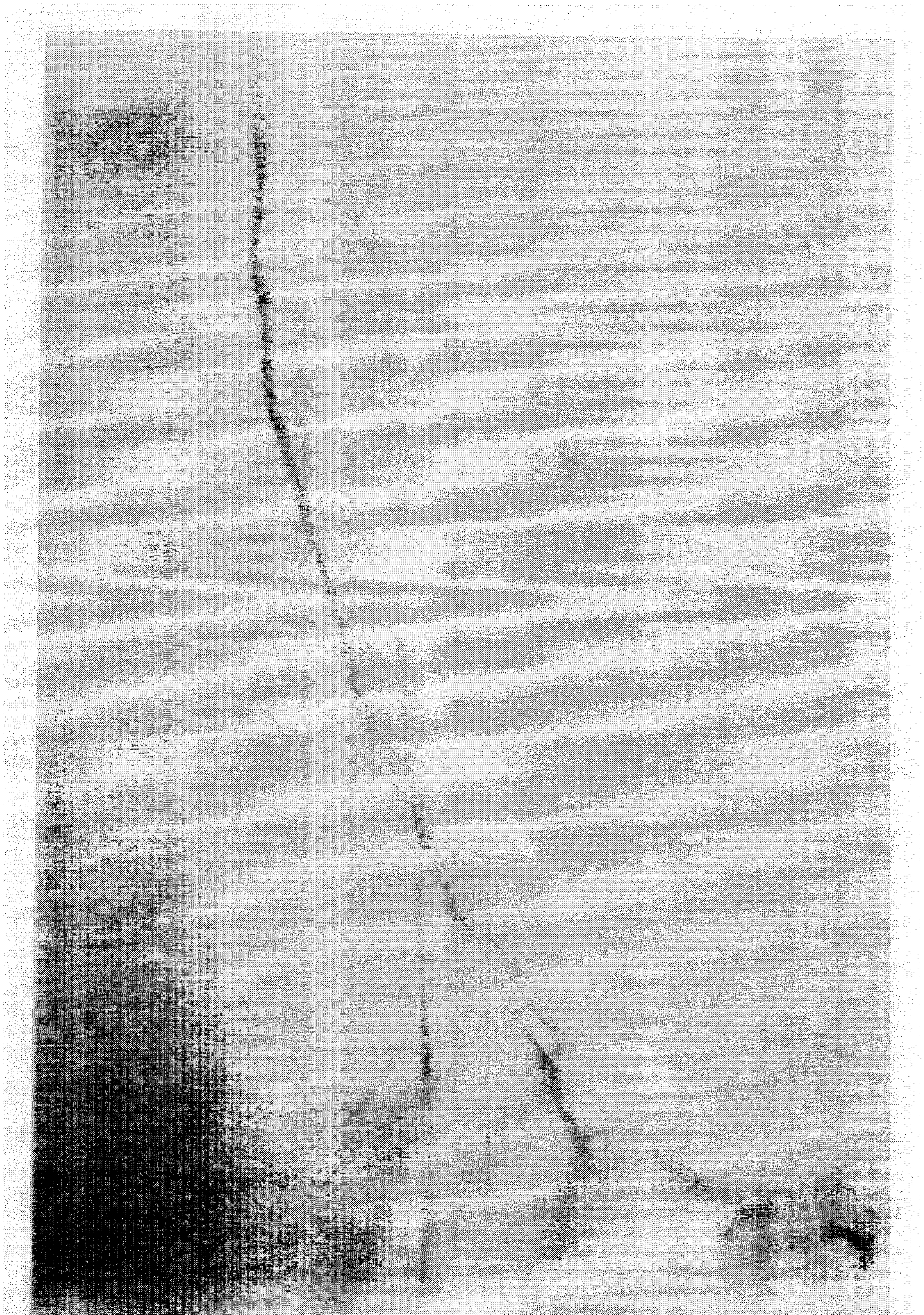
FIG. 13: A light micrograph of the hyphae of LTB (large diameter) penetrated by the hyphae of Trichoderma Biotype 901 (small diameter).

In another set of experiments, the effect of cold tolerant Trichoderma on the hyphae of LTB and *V. dahliae* was investigated. In FIG. 13, the penetration of Trichoderma Biotype 901 into the hypha of LTB is shown in an interference light micrograph. In this Figure, the narrower hypha is of Trichoderma and the wider hypha is of LTB.

Figure 14:
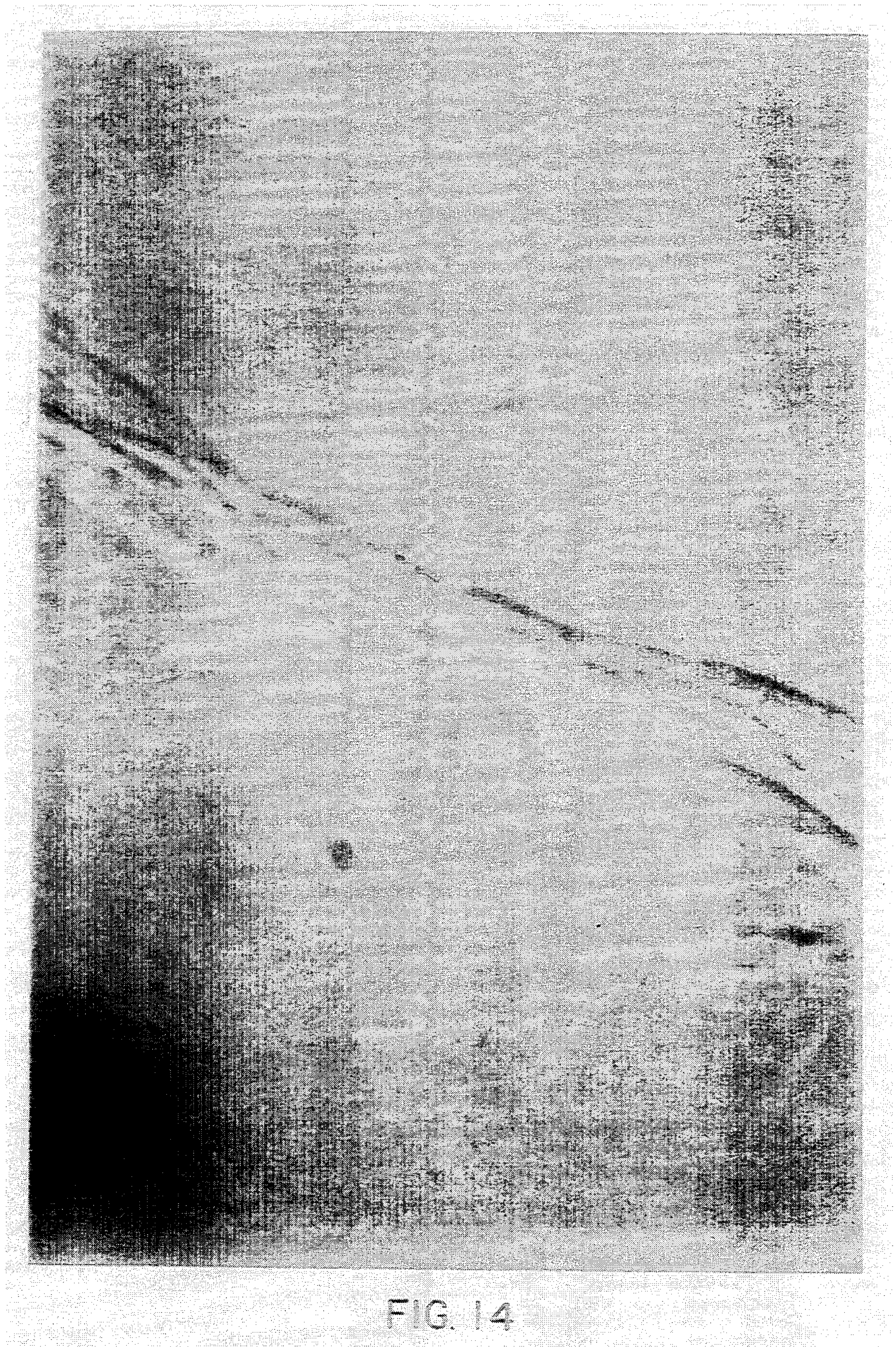
FIG. 14: A light micrograph of the hyphae of *V. dahliae* that has been parasitized by Trichoderma Biotype 603.
Figure 15:
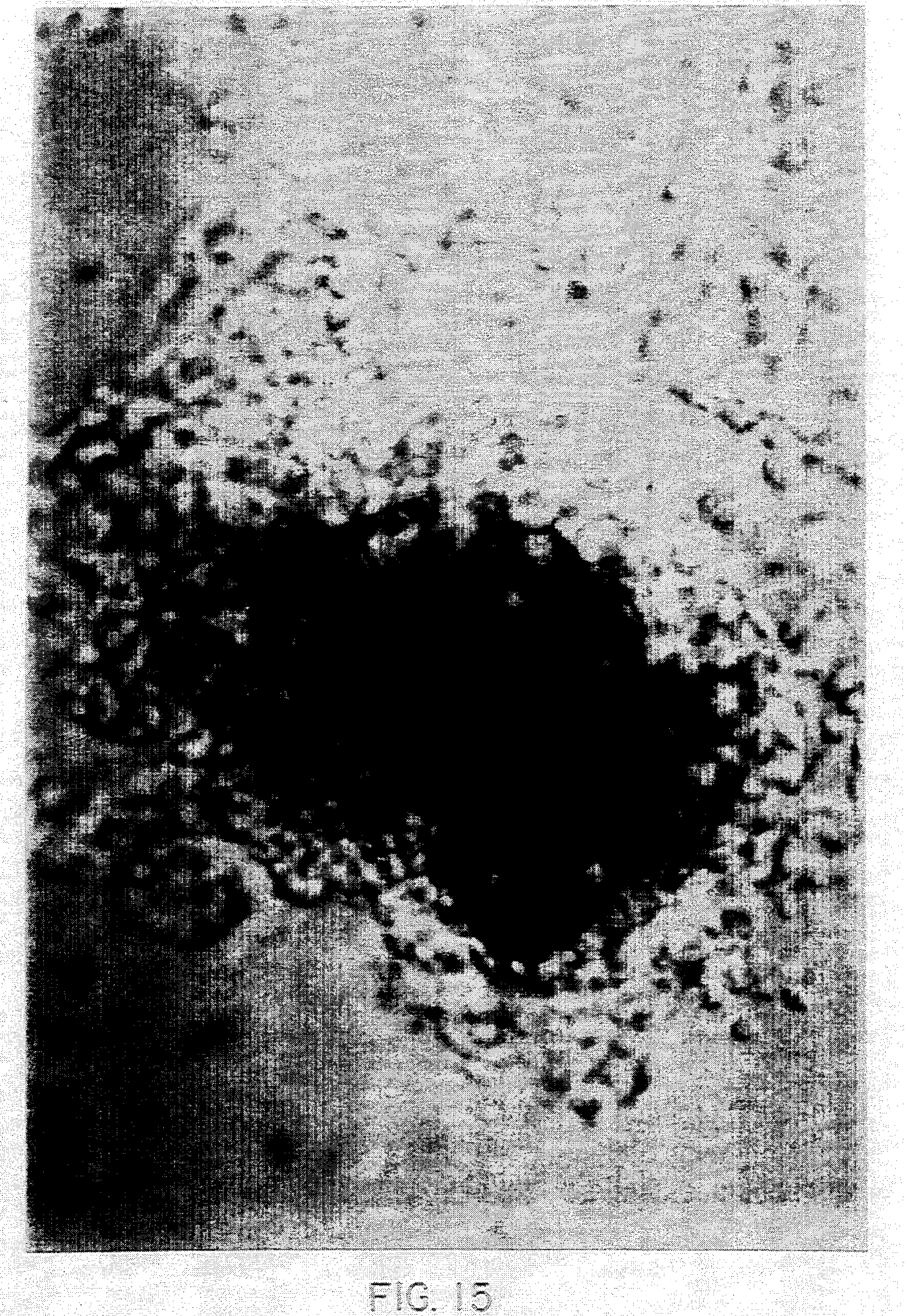
FIG. 15: A light micrograph of the microsclerotia of an unparasitized *V. dahliae.*
Figure 16:
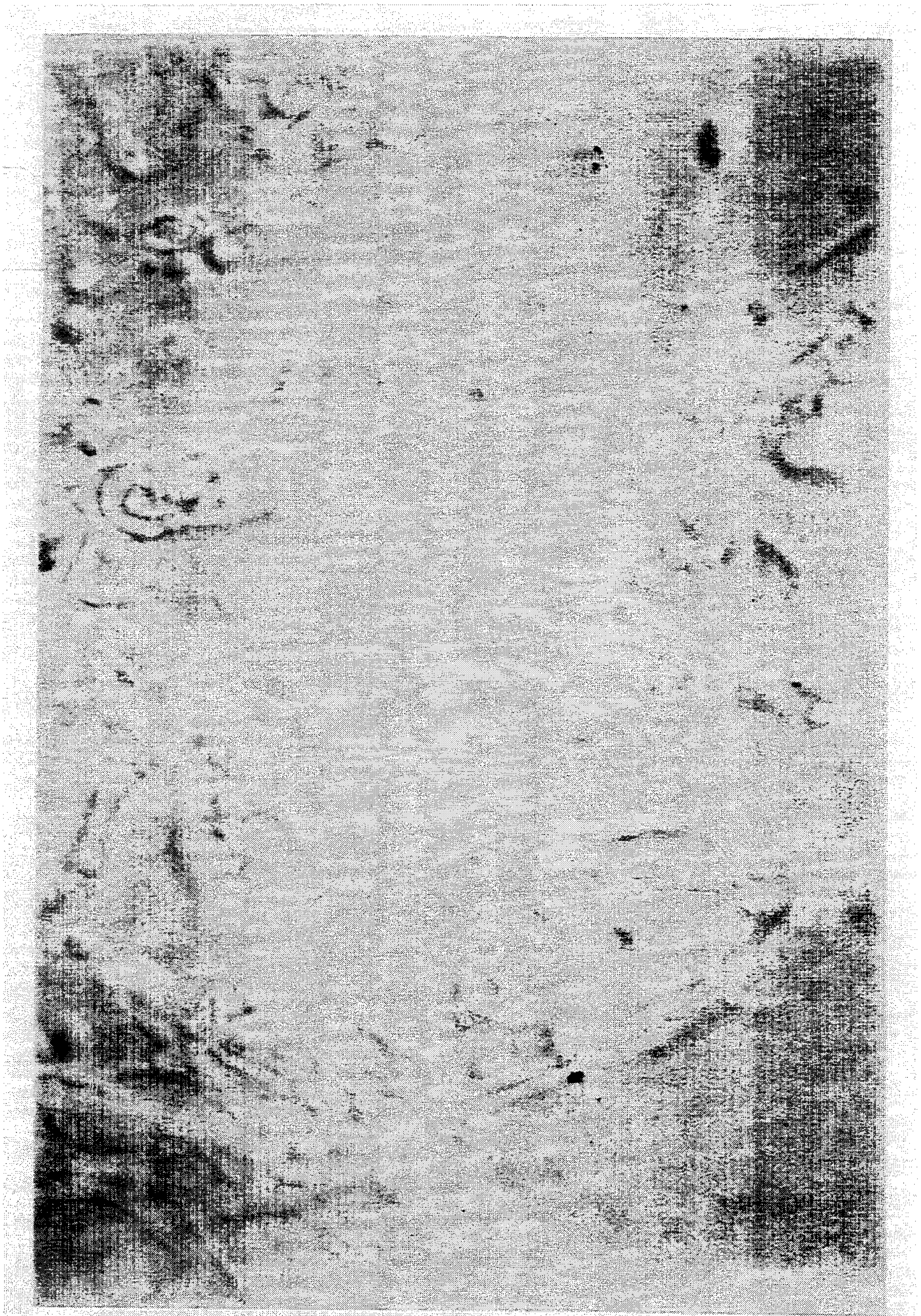
FIG. 16: A light micrograph of the deteriorated mycelia of *V. dahliae* following parasitization by Trichoderma isolate CHS 861 (ATCC 74015).
Figure 17:
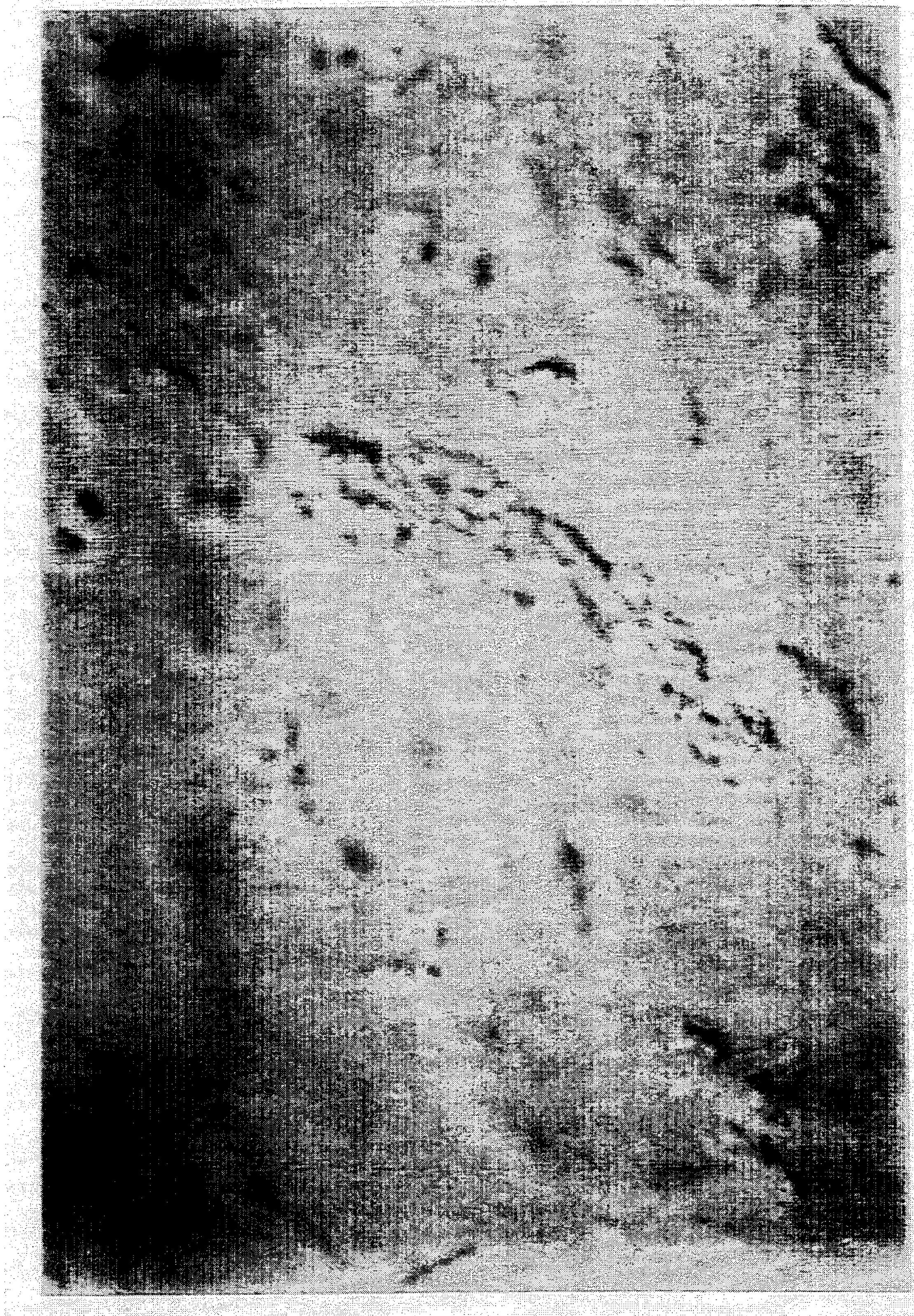
FIG. 17: A light micrograph of the deteriorated microsclerotia of *V. dahliae* following parasitization by Trichoderma isolate CHS 861.

In FIG. 14, the parasitization of the hyphae of *V. dahliae* by Trichoderma Biotype 603 is shown in an interference light micrograph. In this Figure, the *V. dahliae* hyphae are completely parasitized by the cold tolerant Trichoderma. In yet another series of experiments, the effect of cold tolerant Trichoderma on the structural integrity of the microsclerotia and mycelia were investigated. FIG. 15 represents an interference light micrograph of a healthy *V. dahliae* microsclerotia. A healthy microsclerotia is typically dark as shown here. FIG. 17 represents a interference light micrograph of a deteriorated *V. dahliae* microsclerotia following exposure to cold tolerant Trichoderma. The microsclerotia now appears hyaline, which is typical for lysed microsclerotia. FIG. 16 represents a interference light micrograph of the mycelia of *V. dahliae* that has been lysed by cold tolerant Trichoderma.

EXAMPLE 14

The 21 kDa heat stable protein that is useful for controlling fungal pathogens [hereinafter the 21 kDa fungicidal protein] can be cloned and expressed in a heterologous host cell. In a preferred embodiment of the present invention, a nucleic acid probe useful for the identification of the gene encoding the 21 kDa fungicidal protein can be prepared in the following manner. The 21 kDa fungicidal protein can be purified by conventional laboratory techniques. These techniques include but are not limited to ammonium sulfate precipitation, polyethylene glycol treatment, gel filtration chromatography, and ion exchange chromatography. In an especially preferred embodiment, Trichoderma culture filtrates are obtained by filtering about a 10 day old culture through a 0.45 μm filter. The 21 kDa fungicidal protein can be fractionated through a fine grade, Sephadex G-75 gel filtration column. Fractions found to inhibit the growth of sLTB are identified. The protein can be concentrated by polyethylene glycol treatment and further purified by HPLC. The resulting protein is sufficiently pure to obtain an unambiguous amino acid sequence.

The amino acid sequence of at least a portion of the 21 kDa fungicidal protein can be determined using techniques well known to one of ordinary skill in the art. For example, the N-terminal amino acid sequence of the 21 kDa fungicidal protein may be obtained on an Applied Biosystems Inc. 470A protein sequencer. Based upon the identified amino acid sequence, a corresponding nucleotide sequence that is capable of encoding the amino acid sequence can be predicted and a nucleic acid can be constructed synthetically based upon the predicted sequence. Because of the degeneracy of the genetic code, however, prediction of the nucleotide sequence on the basis of the amino acid sequence may lead to several possible nucleotide sequences. A collection of different nucleic acid sequences that comprise the various possible nucleotide sequences can be constructed, labeled and used to screen a DNA library containing the 21 kDa fungicidal protein gene.

A DNA library can be obtained from a cold tolerant Trichoderma culture using standard techniques. In particular, DNA can be obtained from Trichoderma as described by Junghans and Metzkaff, BioTechniques 8:176 (1990). The size of the DNA obtained can be analyzed by conventional gel electrophoresis, e.g. according to Maniatis et al., Molecular Cloning, Cold Spring Harbor, N.Y. 1982, or according to Schlief et al., Practical Methods in Molecular Biology, Springer-Verlag, Inc. N.Y. 1981.

The DNA isolated from the Trichoderma culture can be subjected to partial digestion by restriction endonucleases to obtain a pool of fragments from which structural genes can be cloned. The restriction enzyme used depends on the size of the DNA fragments to be obtained. A preferred restriction enzyme is SauIIIA.

A suitable vector capable of carrying the DNA fragments obtained in a non-essential region of its DNA and capable of replicating in a host cell can be ligated to the DNA fragments to generate a library of recombinant DNA molecules. In the context of the present invention, a vector that is suitable for use is a plasmid or a virus (e.g. bacteriophage) that is capable of being transferred into a host cell or of infecting a host cell and of replicating in a host cell.

In a preferred embodiment of the present invention, a cDNA library, instead of a genomic DNA library, is constructed using mRNA isolated from total RNA. Total RNA may be obtained from a Trichoderma culture using conventional laboratory techniques.

The isolation of mRNA from the total RNA capitalizes on the presence of a poly A tail at the 3′ end of the mRNA. The 3′ tail is used to separate the mRNA from the other RNA species. Separation is achieved by chromatography on an oligo dT cellulose column by binding of the poly A tail of mRNA with the T residues on the cellulose column. The unbound RNA can be washed free of the column and the mRNA can be eluted by conventional buffers that destabilize the A-T duplex. The RNA concentration is then determined spectrophotometrically.

The integrity of the mRNA preparation, e.g. whether it is full-length or simply a small fragment with a 3′ poly A tail, can be determined by in vitro translation of the mRNA. Full-length mRNAs are selected and used to construct a cDNA library. The method by which a cDNA library can be constructed from mRNA is well known to one of ordinary skill in the art. For example, the method described by Maniatis et al., supra, can be employed. Specifically, the isolated mRNA can be employed as a template for the synthesis of a first strand of cDNA molecules using reverse transcriptase. The first strand cDNA molecules are, in turn, used as template for the synthesis of a second-strand of cDNA, utilizing an enzyme such as DNA polymerase I.

To find the nucleotide sequence in the cDNA library that encodes the 21 kDa fungicidal protein, a complementary nucleic acid probe is employed that contains the predicted nucleotide sequence based upon the partial amino acid sequence of 21 kDa fungicidal protein. In the alternative, polyclonal or monoclonal antibodies to the fungicidal protein can be produced in experimental animals or in hybridomas, respectively, and used to identify transformed host cells that produce the 21 kDa fungicidal protein.

In a preferred embodiment of the present invention, at least a portion of the amino acid sequence of the purified 21 kDa fungicidal protein is determined by amino acid sequencing. Nucleic acid probes based upon the predicted nucleotide sequence can be constructed in accordance with conventional laboratory techniques. In formulating the sequences to be constructed, different strategies can be adopted.

Where nucleotides are ambiguous at a number of locations, the ambiguity can be circumvented by synthesizing mixtures of nucleotides that represent every codon combination. Where codon ambiguity is excessive, however, alternative strategies can be employed. In one embodiment of the present invention, groups of mixed oligonucleotides are synthesized where the ambiguity is held to a minimum within each group and the combination of sequences among the groups represent all possible coding combinations. For example, a collection of short nucleic acid sequences can be made, each sequence containing about 15 to 20 bp and representing every possible codon combination. In another embodiment of the present invention, long nucleic acid sequences, e.g., ones that have about 30 to about 60 bp with minimal mismatch base pairs, can also be designed. The synthesis of these nucleotides is exemplified in, e.g., Suggs et al., *Proc. Natl. Acad. Sci*, 78:6613–6617 (1981), Ullrich et al., *EMBO J.*, 3:361–364 (1984), Shah et al., *Science*, 233:478–481 (1986), and Lathe R., *J. Mol. Biol.*, 183:1–12 (1985), Ohtsuka et al., *J Biol. Chem.* 260:2605–2608 (1985), Martin & Castro, *Nucleic Acid Res.* 13:8927–8938 (1985).

In as yet another embodiment of the present invention, probes can be designed using base analogs at ambiguous codon positions that form base pairs with the natural bases without destabilizing duplex formation. In particular, 2-deoxyinosine can be used since it can form a base pair at A/C or G/T. Ambiguities and the instability produced is not large enough to cause problems with duplex formation.

Alternatively, a base analog with an increased hybridization potential, e.g., 2-amino-2-deoxyadenosine, can be substituted for a normal base within a probe. This 2-amino-2-deoxyadenosine can pair with T residues and form three hydrogen bonds instead of the normal two hydrogen bonds. This bonding results in additional duplex stability compensating for the disruptive effects of ambiguity at the degenerative positions in codons. Incorporating two or more of these methods is also a viable approach to generating a probe. The end result of any combination of these techniques would be a nucleic acid sequence specific for the gene of interest.

A nucleic acid probe for the detection of the 21 kDa fungicidal protein gene can be modified to detect extremely small amounts of the gene, e.g., by labeling the probe with [32P]-phosphate at the 3' or 5' end, or with biotin moieties by a variety of conventional techniques as in, e.g., Rigby et al., *J. Mol. Biol.*, 113:237–251 (1977), Murasugi et al., DNA. 3:269–277 (1984), and Haas et al., *Nucleic Acid Res.*, 14:3976 (1986). The radioactive labeling can be performed using commercially available 3' or 5' end labeling kits from, e.g., Amersham Corporation (Arlington Heights, Ill.) or New England Nuclear (Boston, Mass.), and following the manufacturer's directions. The 21 kDa fungicidal protein gene in the DNA library can then be identified by hybridization with the labeled probe.

In a specific embodiment of the present invention, a recombinant lambda phage containing a Trichoderma cDNA library, as described supra, is screened substantially according to the method of Maniatis et al., loc. cit., using a [32P]-labelled 21 kDa fungicidal protein specific oligonucleotide probe. Hybridization is carried out at 37° C. to 42° C. for 16 to 24 hours, after which the filters are washed at either 42° C., or 65° C. The membranes are autoradiographed to identify the hybrid vectors that carry the 21 kDa fungicidal protein gene.

DNA that reacts positively with the 21 kDa fungicidal protein specific probe can be isolated and the 21 kDa fungicidal protein gene isolated and ligated to another vector. For example, if a lambda gt11 phage vector is used, the desired DNA can be removed from the vector by EcoRI digestion, as the cDNA had been inserted into the phage vector at an EcoRI restriction site.

The gene encoding the 21 kDa fungicidal protein is then subcloned into another plasmid in order to produce large quantities of the gene. In a specific embodiment of the present invention, the genes are subcloned into the plasmid pBR322 and maintained in *E. coli.* The *E. coli* cells containing the pBR322 plasmid with an insert containing the 21 kDa fungicidal protein gene is propagated to produce large quantities of the gene. This DNA can be extracted from the transformed host using conventional techniques well known to the person of ordinary skill.

In another embodiment of the present invention, the DNA fragment that contains the 21 kDa fungicidal protein gene can be ligated to a suitable promoter so as to place the gene under the control of that promoter. A suitable promoter is one that is capable of functioning in a transformed host. For example, if the host to be transformed is a plant, 21 kDa fungicidal protein gene can be ligated to a plant promoter, such as Pnos, the promoter for nopaline synthetase; if the host to be transformed is a bacterium, the 21 kDa fungicidal protein gene can be ligated to a bacterial promoter, such as the trp, lac, or tac promoter of *E. coli.* In the alternative, the 21 kDa fungicidal protein gene can be ligated to a virus promoter, such as the 16S and 35S promoter of cauliflower mosaic virus.

The promoter must be "operably linked" to the 21 kDa fungicidal protein gene. In the context of this invention, "operably linked" refers to the proper location of the promoter relative to the structural gene so that the promoter and gene are in proper orientation, position and reading frame to permit high levels of transcription and translation of the biologically active 21 kDa fungicidal protein upon induction in a transformed host. The choice of a promoter and the DNA sequence surrounding the promoter will be governed by the effect of this sequence on expression in a transformed host.

In another specific embodiment of the instant invention, the 21 kDa fungicidal protein gene can be linked to another structural gene to express a fusion protein in a transformed host. Such a fusion protein comprises the 21 kDa fungicidal protein covalently linked to a second polypeptide. For example, the fusion protein can be a portion of the *E. coli* protein β-galactosidase linked to the fungicidal protein. When the fungicidal protein is expressed as a fusion protein, the gene encoding the fusion protein must be operably linked to a suitable promoter in a suitable vector. Additionally, the gene encoding the 21 kDa fungicidal protein must be in the same reading frame as the second polypeptide.

A vector containing the gene encoding 21 kDa fungicidal protein operably linked to a suitable promoter can be employed to transform a suitable host using conventional techniques. A suitable transformed host is one that is capable of expressing the 21 kDa fungicidal protein DNA sequence. In a preferred embodiment, a suitable transformed host is incapable of producing the 21 kDa fungicidal protein in a significant amount before transformation and becomes capable of producing 21 kDa fungicidal protein in a significant amount after transformation. Such a host can be a plant, a bacterium or a fungus. The plant host can be an annual plant, such as tobacco species or a grass species, or a perennial plant species. The bacterium can be any bacterium, e.g., *E. coli*, a Bacillus species or an Agrobacterium species. The fungus is selected from the group consisting of a lactarius species, an Aspergillus species, and a Trichoderma species.

The transformed cell is cultured in a suitable media to express the 21 kDa fungicidal protein. The 21 kDa fungicidal protein can be isolated using standard procedures. The protein preparation obtained is generally free of other Trichoderma proteins.

The same procedure can be followed to clone and express the 17 kDa and the 5–10 kDa fungicidal proteins associated with cold tolerant Trichoderma from purified preparations of these proteins.

The 17 kDa protein can be purified from cold tolerant Trichoderma culture filtrates as follows by gel filtration using HPLC. In an especially preferred embodiment, a C-18 gel filtration column is used.

The 5–10 kDa antimycotic molecule can be purified from cold tolerant Trichoderma culture filtrates as follows. The protein is initially purified by ultrafiltration as described supra and further purified by gel filtration using HPLC.

What is claimed is:

1. A biologically pure cold-tolerant Trichoderma isolate, wherein said isolate is CHS 861 (ATCC 74015).

2. A mutant of the cold-tolerant Trichoderma isolate as claimed in claim 1, wherein said mutant is Benomyl resistant.

3. A mutant as claimed in claim 2, wherein said mutant is selected from the group consisting of Biotype 453

(ATCC 74016), Biotype 603 (ATCC 74018), and Biotype 901 (ATCC 74017).

4. A pure mutant as claimed in claim 2, wherein said mutant is Biotype 453 (ATCC 74016).

5. A mutant as claimed in claim 2, wherein said mutant is Biotype 603 (ATCC 74018).

6. A mutant as claimed in claim 2, wherein said mutant is Biotype 901 (ATCC 74017).

* * * * *